「

US010752879B2

(12) United States Patent
Ejiri et al.

(10) Patent No.: US 10,752,879 B2
(45) Date of Patent: *Aug. 25, 2020

(54) CULTURE METHOD AND CELL CLUSTER

(71) Applicants: Corning Incorporated, Corning, NY (US); Public University Corporation Yokohama City University, Yokohama-shi (JP)

(72) Inventors: Yoko Ejiri, Tsukuba (JP); Hideki Taniguchi, Yokohama (JP); Takanori Takebe, Yokohama (JP)

(73) Assignees: Corning Incorporated, Corning, NY (US); Public University Corporation Yokohama City University, Yokohma-Shi, Kanagawa (JP)

(*) Notice: Subject to any disclaimer, the term of this patent is extended or adjusted under 35 U.S.C. 154(b) by 132 days.

This patent is subject to a terminal disclaimer.

(21) Appl. No.: 15/314,653

(22) PCT Filed: May 29, 2015

(86) PCT No.: PCT/JP2015/002738
§ 371 (c)(1),
(2) Date: Nov. 29, 2016

(87) PCT Pub. No.: WO2015/182159
PCT Pub. Date: Dec. 3, 2015

(65) Prior Publication Data
US 2017/0183621 A1    Jun. 29, 2017

(30) Foreign Application Priority Data

May 30, 2014  (JP) .................................. 2014-112959

(51) Int. Cl.
C12N 5/00       (2006.01)
C12N 5/077      (2010.01)
C12N 5/071      (2010.01)
C12N 5/10       (2006.01)
C12N 1/00       (2006.01)

(52) U.S. Cl.
CPC ............ *C12N 5/0062* (2013.01); *C12N 1/00* (2013.01); *C12N 5/069* (2013.01); *C12N 5/0652* (2013.01); *C12N 5/0671* (2013.01); *C12N 5/0697* (2013.01); *C12N 5/10* (2013.01); C12N 2502/1352 (2013.01); C12N 2506/45 (2013.01); C12N 2513/00 (2013.01); C12N 2531/00 (2013.01); C12N 2533/30 (2013.01)

(58) Field of Classification Search
None
See application file for complete search history.

(56) References Cited

U.S. PATENT DOCUMENTS

| 6,284,451 B1 | 9/2001 | Funatsu et al. | |
|---|---|---|---|
| 9,127,255 B2 | 9/2015 | Jensen | |
| 2010/0068793 A1 | 3/2010 | Ungrin et al. | |
| 2011/0165609 A1* | 7/2011 | Ramsing | C12M 21/06 435/29 |
| 2014/0227784 A1* | 8/2014 | Ejiri | C12M 23/12 435/402 |
| 2014/0289877 A1* | 9/2014 | Taniguchi | A61K 35/28 800/8 |

FOREIGN PATENT DOCUMENTS

| JP | 9-56814 A | 3/1997 | |
|---|---|---|---|
| JP | 2001-509272 A | 7/2001 | |
| JP | 2004-166717 A | 6/2004 | |
| JP | 2005027598 A | 2/2005 | |
| JP | 2010088347 A | 4/2010 | |
| JP | 2014112959 A | 6/2014 | |
| WO | 98/31466 A1 | 7/1998 | |
| WO | WO-9831466 A1 * | 7/1998 | ............ B01L 3/5085 |
| WO | 2007/058105 A1 | 5/2007 | |
| WO | 2008/130025 A1 | 10/2008 | |
| WO | WO-2008130025 A1 * | 10/2008 | ............ C12M 23/12 |
| WO | 2012036011 A1 | 3/2012 | |
| WO | 2013/042360 A1 | 3/2013 | |
| WO | 2013/047639 A1 | 4/2013 | |
| WO | WO-2013047639 A1 * | 4/2013 | ............ A61K 35/28 |

(Continued)

OTHER PUBLICATIONS

International Search Report dated Sep. 1, 2015 in PCT/JP2015/002738 filed May 29, 2015.
Maya Schuldiner et al., "Effects of eight growth factors on the differentiation of cells derived from human embryonic stem cells", Proceedings of the National Academy of Sciences, vol. 97, No. 21, Oct. 10, 2000, 7 pages.
K. Xue et al., "A Two-Step Method of Constructing Mature Cartilage Using Bone Marrow-Derived Mesenchymal Stem Cells", Cells Tissues Organs, vol. 197, No. 6, Jul. 2013, 2 pages (Abstract only).
Extended European Search Report dated Dec. 18, 2017 in corresponding European Patent Application No. 15799890.7, 8 pages.
Written Opinion and Search Report dated Nov. 14, 2017 in corresponding Singaporean Patent Application No. 11201609916R, 12 pages.

(Continued)

*Primary Examiner* — Nghi V Nguyen
(74) *Attorney, Agent, or Firm* — Annie J. Kock; Therese Finan

(57) ABSTRACT

The present invention provides a culture method for culturing, in recesses (10), a population including two or more cells including a cell derived from a stem cell and a mesenchymal cell. The cell derived from a stem cell is a cell obtained by differentiating a stem cell in vitro. The cell is a cell of one or more types selected from the group consisting of an endodermal cell, an ectodermal cell, and a mesodermal cell. The population is cultured in the recesses (10) together with a vascular cell or a secretor factor. Each recess (10) includes a space in which cells are movable. When a volume of the space is represented by V mm$^3$ and the number of mesenchymal cells seeded in the space is represented by N, V is 400 or less and N/V is in a range from 35 to 3000.

14 Claims, 13 Drawing Sheets

(56) References Cited

FOREIGN PATENT DOCUMENTS

WO   WO 2014/196204 A1   12/2014
WO   WO 2014/199622 A1   12/2014

OTHER PUBLICATIONS

Takanori Takebe et al., "Vascularized and functional human liver from an iPSC-derived organ bud transplant", Nature, Letter, doi :10.1038/nature12271, XP007922049, Jan. 1, 2013, pp. 1-5.
Takanori Takebe et al., "Generation of a Vascularized and Functional Human Liver from an iPSC-derived Organ Bud Transplant", Nature Protocol, vol. 9, No. 2, XP055166485, Jan. 23, 2014, pp. 396-409.
Curcio et al. "Mass transfer and metabolic reactions in hepatocyte spheroids cultured in rotating wall gas-permeable membrane system", Biomaterials 28 (2007) pp. 5487-5497.
Pampaloni et al. "The third dimension bridges the gap between cell culture and live tissue" Nature Reviews Molecular Cell Biology 8(2007) pp. 839-845.
Peters et al. "Antimicrobial Peptides: Primeval Molecules or Future Drugs?" PLoS One 30;5(12): e15689. 2010, 4 pgs.
Rimann et al. "Synthetic 3D multicellular systems for drug development", Current Opinion in Biotechnology, 2012 (23) pp. 1-7.
Joo et al. "Angiopoietin-1 promotes endothelial differentiation from embryonic stem cells and induced pluripotent stem cells", Blood. 25;118 (8): pp. 2094-2104. 2011.
Machine Translation of JP2016523166 Office Action dated Jan. 8, 2019, Japan Patent Office, 3 Pgs.
Ruedel et al; "Development of a Model System to Analyze Chondrogenic Differentiation of Mesenchymal Stem Cells"; Int J Clin Exp Pathol (2013), vol. 6, No. 12, pp. 3042-3048.
Takebe et al; "Generation of a Vascularized and Functional Human Liver From an iPSC-Derived Organ Bud Transplant"; Nat Protoc (2014), vol. 9, No. 2, pp. 396-409.
Benz et al; "Maintenance of "Stem Cell" Features of Cartilage Cell Sub-Populations During in Vitro Propagation"; J Transl Med (2013), vol. 11, Article No. 27, pp. 1-23.
Choi et al; "Controlled-Size Embryoid Body Formation in Concave Microwell Arrays"; Biomaterials (2010), vol. 31, pp. 4296-4303.
Cook et al; "Micromarrows—Three-Dimensional Coculture of Hematopoietic Stem Cells and Mesenchymal Stromal Cells"; Tissue Eng Part C (2012), vol. 18, No. 5, pp. 319-328.
Enomoto et al; "Self-Formation of Vascularized Hepatic Tissue From Human Adult Hepatocyte"; Transplant Proc (2014), vol. 46, pp. 1243-1246.
Goldring et al; "Assessing the Safety of Stem Cell Therapeutics"; Cell Stem Cell (2011), vol. 8, pp. 618-628.
Hsu et al; "Microwell Chips for Selection of Bio-Macromolecules That Increase the Differentiation Capacities of Mesenchymal Stem Cells"; Macromol Biosci (2013), vol. 13, pp. 1100-1109.
Japanese Patent Application No. 2019-132353 Office Action dated Jun. 30, 2020; 9 Pages; Japanese Patent Office.
Takebe et al; "Vascularized and Functional Human Liver From an iPSC-Derived Organ Bud Transplant"; Nature (2013), vol. 499, pp. 481-485.

* cited by examiner

CULTURE METHOD AND CELL CLUSTER

TECHNICAL FIELD

The present invention relates to a culture method for culturing a stem cell to obtain a cell cluster. The stem cell is, for example, an undifferentiated cell of an induced pluripotent stem cell or an embryonic stem cell. The present invention also relates to a cell cluster obtained by the culture method.

BACKGROUND ART

In recent years, attempts have been made to use artificially differentiated pluripotent stem cells for drug discovery screening and regenerative medicine (e.g., Non Patent Literature 1). The pluripotent stem cells described herein refer to cells which have an ability to differentiate into various functional cells. The pluripotent stem cells are caused to differentiate into cells having functions specific to a certain organ or cell type depending on what is the purpose of drug discovery screening or regenerative medicine. For example, iPS cells are used as the pluripotent stem cells. However, in many cases, the artificially differentiated pluripotent stem cells are capable of reproducing only a part of vital functions in vivo. Accordingly, the functions of the artificially differentiated pluripotent stem cells are much lower than the functions of cells in vivo.

In drug discovery screening tests using cells, the cells show drug susceptibility and toxic reaction. It is required to show drug susceptibility and toxic reaction that are similar to those obtained in a test performed in a living body, that is, a so-called in vivo test. The above-mentioned prior art is insufficient for using pluripotent stem cells artificially differentiated for such an application. Therefore, there is a demand for differentiating pluripotent stem cells to more mature cells. The more mature cells described herein refer to cells having functions whose expression level is equivalent to that of functions of cells in vivo.

In the field of conventional medicine, organ transplantation and artificial organ transplantation are carried out. However, there are problems with the transplantations such as shortage of donors and transplant rejection. For example, in clinical practice, organ transplantation and replacement with artificial organs are carried out to treat severe organ failures. However, the organ transplantation and artificial organ transplantation have some fundamental problems that have not been solved. There are problems with organ transplantations such as rejections and critical shortage of donors, and artificial organs are only capable of replacing some of the functions of an organ for a limited period of time (e.g., Patent Literature 1 and 2).

On the other hand, in the field of regenerative medicine, artificial creation of human tissues is carried out. A method is known in which terminally differentiated cells are seeded on a support or scaffolding for this creation. Further, in recent years, a method for preparing a tissue and an organ (Patent Literature 3) and a method for preparing islet cells by inducing undifferentiated cells (Patent Literature 4) have been disclosed.

Patent Literature 3 discloses a method for co-culturing a mesenchymal cell, an organ cell, and a vascular endothelial cell, thereby producing a cell cluster which is called an organ bud. The organ bud grows into an organ and can be transplanted in a living body. An organ bud produced by this method is an extremely favorable implant. On the other hand, there is a risk that when the organ bud is transplanted, a cell in the organ bud may differentiate into a cell of an organ other than the transplantation target (Non Patent Literature 2). A cell of an organ other than the transplantation target refers to a cell other than a cell of the organ into which the organ bud grows. Examples of this cell include a fibrous cell and a bone cell. Accordingly, there is a demand for minimizing the risk that a cell in an organ bud differentiates into a cell of an organ other than the transplantation target.

CITATION LIST

Patent Literature

[Patent Literature 1] Japanese Unexamined Patent Application Publication No. H09-56814
[Patent Literature 2] Japanese Unexamined Patent Application Publication No. 2004-166717
[Patent Literature 3] International Patent Publication No. WO 2013/047639
[Patent Literature 4] International Patent Publication No. WO 2007/058105

Non Patent Literature

[Non Patent Literature 1] Maya Schuldiner, et. al., "Effects of eight growth factors on the differentiation of cells derived from human embryonic stem cells", PNAS, 97 vol 21, Oct. 10, 2000 (Published online), pp. 11307-11312
[Non Patent Literature 2] Xue K., et. al., "A Two-Step Method of Constructing Mature Cartilage Using Bone Marrow-Derived Mesenchymal Stem Cells", Cells Tissues Organs 2013; 197, June 2013, pp. 484-495

SUMMARY OF INVENTION

Technical Problem

Techniques related to Patent Literature 3 are used for regenerative medicine or evaluation of drugs, and thus it is required to improve functions per a unit of organ bud. Further, in the practice of regenerative medicine, it is required to develop a safe artificial tissue. It is required that the artificial tissue not differentiate into a tissue of an organ other than the transplantation target.

Additionally, there is another requirement that the cost required for culturing a large number of organ buds be reduced. In this case, development of a culture method to achieve a reduction in cost is a problem to be solved. In the culture method, it is necessary to improve functions per organ bud to reduce the number of cells used as various materials necessary for transplantation. It is also necessary to reduce the time and culture medium required to allow cells to be differentiated into a desired organ bud.

Further, the mesenchymal stem cell included in the mesenchymal cell differentiates into various tissues. Accordingly, when an organ bud is transplanted into a bone or fibrous tissue, there is a possibility that the differentiation of the mesenchymal stem cell may advance in the transplanted site (Non Patent Literature 2). A problem to be solved by the culture method is to reduce the risk of unexpected differentiation.

As described above, there is a demand for a method for efficiently obtaining a cell cluster having functions closer to those of a biological tissue. The cell cluster is required to be safe and, especially, not to differentiate into a tissue of an organ other than the transplantation target.

Solution to Problem

The present inventors have invented a method for obtaining a cell cluster. The cell cluster is a cell cluster that has not been achieved in the past. The cell cluster has functions similar to those in vivo and is also safe. In the method, when a cell is cultured to obtain a cell cluster, the ratio of mesenchymal cells is reduced as compared with the conventional ratio. This is because the mesenchymal cell is more likely to form a tissue of an organ other than the transplantation target. The present inventors have found the density appropriate for the mesenchymal cell in the method.

A culture method according to an aspect of the present invention is a culture method for culturing, in a predetermined area, a population including two or more cells including a cell derived from a stem cell and a mesenchymal cell. The cell derived from a stem cell is a cell of one or more types selected from the group consisting of an undifferentiated endodermal cell, an undifferentiated ectodermal cell, and an undifferentiated mesodermal cell.

The population is preferably cultured in the above area together with at least one of a vascular cell, a factor autonomously secreted from a vascular cell, and a factor secreted from a vascular cell due to the presence of both a vascular cell and a mesenchymal cell.

The above area is formed of a space in which cells are movable. The volume of the space is represented by V mm$^3$. The number of the mesenchymal cells seeded in the space is represented by N. At this time, the V is equal to or less than 400. Further, N/V is in a range from 35 to 3000. This culture method is suitable for obtaining a cell cluster from the population.

The present inventors have limited the volume of the space, in which cells during culture (cells to be cultured) are movable, within a predetermined range. The present inventors have also limited the number of mesenchymal cells to be included in the space, in which the cells are movable, within a predetermined range. Thus, the present inventors have found that a cell cluster having functions similar to those in vivo as compared with that of the conventional cell cluster can be obtained from the above-mentioned cells. The present inventors have also found that the cell cluster does not differentiate into a tissue of an organ other than the transplantation target.

As described above, the culture method with which a cell cluster has can be obtained is achieved. Additionally, the culture method does not use any complicated technique. This leads to a reduction in cost of preparing cells.

The ratio of the number of the mesenchymal cells to the total number of cells used for culture is preferably 0.5% or more but less than 5%. The population is preferably formed of a cell number X of the cells derived from a stem cell and a cell number Y of the mesenchymal cells. The X:Y is preferably in a range from 20:1 to 100:1. In this case, the cell number (X) of the cells derived from a stem cell is the total number of cells selected from the group consisting of an endodermal cell, an ectodermal cell, and a mesodermal cell, which are derived from a stem cell, or a combination thereof.

The above area is preferably formed of a microchamber. The N/V is in a range from 100 to 300. The X:Y is preferably in a range from 20:1 to 50:1. The V is preferably equal to or less than 1. When the equivalent diameter of the microchamber is represented by E and the depth of the microchamber is represented by D, E:D is preferably in a range from 1:0.5 to 1:2.

Since mesenchymal cells are necessary to obtain a cell cluster being similar to those of an object tissue, it is better to use a smaller number of mesenchymal cells. However, when the N/V ratio is equal to or less than 100, it takes a lot of time for differentiation induction, or the level of functions per cell cluster is lowered. On the other hand, when the N/V ratio is equal to or more than 300, the ratio of cells derived from a stem cell, which have a capability to differentiate into an object tissue, is lowered, and the level of functions per cell cluster is lowered. For this reason, the N/V ratio is preferably in a range from 100 to 300.

When the ratio of the mesenchymal cells to the total number of cells used for culture is less than 0.5%, it takes a lot of time for differentiation induction, or the level of functions per cell cluster is lowered. On the other hand, when the ratio of the mesenchymal cells to the total number of cells used for culture is equal to or more than 5%, the ratio of the cells derived from a stem cell, which have a capability of differentiating into an object tissue, decreases, or the level of functions per cell cluster is lowered. For this reason, the ratio X:Y is preferably in a range from 50:1 to 20:1.

Further, when the space in which cells are movable exceeds 1 mm$^3$, the movement distance of the cells increases and it takes a lot of time to form a cell cluster. For this reason, the space in which cells are movable is preferably equal to or less than 1 mm$^3$.

Furthermore, to obtain a cell cluster having functions of an object tissue, it is necessary to efficiently supply nutrients and factors effective for differentiation induction during culture to a cell cluster. Accordingly, it is better to use a shallower microchamber. However, if the microchamber is extremely shallow, a cell cluster moves to adjacent microspaces and the cell clusters are connected to each other. Accordingly, the ratio of the equivalent diameter to the depth is preferably equal to or more than 1:0.5. To supply nutrients in the medium and material for promoting differentiation to a cell cluster, the ratio of the equivalent diameter to the depth is preferably equal to or less than 1:2.

The cell cluster obtained by the three-dimensional culture is preferably an organ bud. The cell cluster obtained by the three-dimensional culture preferably has a spheroid shape, and the diameter of the cell cluster having the spheroid shape is preferably in a range from 20 μm to 2 mm. The cell derived from a stem cell is preferably derived from a fetal stem cell or an induced pluripotent stem cell. The cell derived from a stem cell is preferably derived from an induced pluripotent stem cell. The cell derived from a stem cell is preferably an endodermal cell.

The above area is preferably formed of a microchamber. The equivalent diameter of the microchamber is preferably in a range from 20 μm to 2.5 mm. The depth of the microchamber is preferably in a range from 20 μm to 1000 μm.

The microchamber preferably includes a bottom portion and a horn portion. The horn portion preferably includes a wall. The wall preferably has a taper angle in a range from 1 to 20 degrees. The bottom portion preferably includes a space having a hemispherical shape or a truncated cone shape.

The microchamber preferably has a culture surface in contact with a cell. The culture surface is preferably coated with a polymer selected from the group consisting of a phospholipid, a phospholipid-polymer complex, poly(2-hydroxyethyl methacrylate) (PHEMA), polyvinyl alcohol, agarose, chitosan, polyethyleneglycol, and albumin, or a combination thereof.

A cell cluster according to an embodiment of the present invention is a cell cluster obtained by culturing, in a predetermined area, a population including two or more cells including a cell derived from a stem cell and a mesenchymal cell. The cell derived from a stem cell is a cell obtained by differentiating a stem cell in vitro, and is one or more types of cells selected from the group consisting of an endodermal cell, an ectodermal cell, and a mesodermal cell.

The population is cultured together with at least one of a vascular cell, a factor secreted from a vascular cell, and a factor secreted from a mesenchymal cell due to the presence of both a vascular cell and a mesenchymal cell.

The above area is formed of a space in which cells are movable. The volume of the space is represented by V mm$^3$. The number of the mesenchymal cells seeded in the space is represented by N. At this time, the V is equal to or less than 400. Further, N/V is in a range from 35 to 3000.

The population is preferably formed of the cell number X of the cells derived from a stem cell and the cell number Y of the mesenchymal cells. The X:Y is preferably in a range from 20:1 to 100:1.

Advantageous Effects of Invention

According to an embodiment, it is possible to provide a method for efficiently culturing a cell cluster having functions similar to those of a biological tissue. The cell cluster is characterized by being safe, and more particularly, is characterized by not differentiating into a tissue of an organ other than a transplantation target.

DESCRIPTION OF EMBODIMENTS

Figure 1:
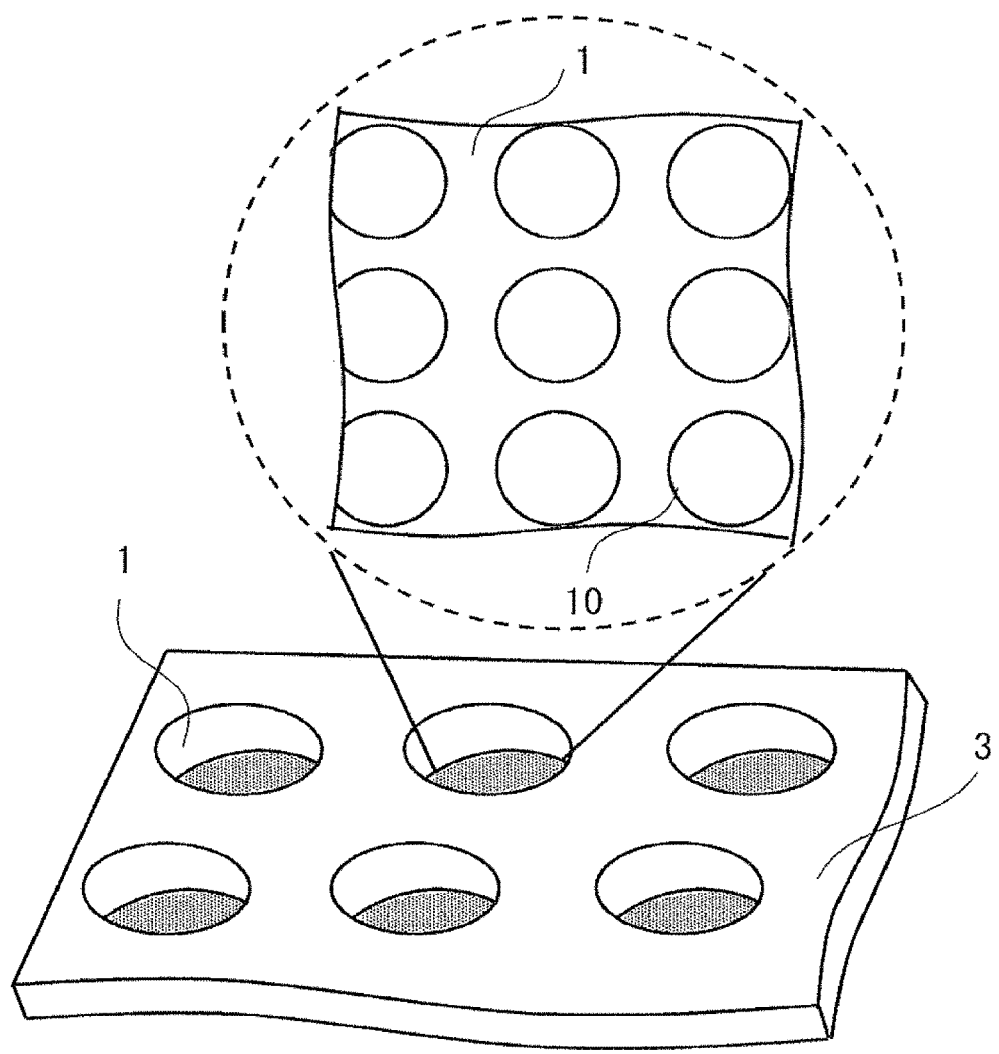
FIG. 1 is a diagram showing an example of a culture chamber according to an embodiment.

Embodiments will be described below with reference to the drawings. To clarify the explanation, omissions and simplifications are made as necessary in the following description and the drawings. Throughout the drawings, the constituent elements having the same configuration or function, or corresponding parts are denoted by the same reference numerals, and the descriptions thereof are omitted.

A culture method according to an embodiment relates to a method for preparing a cell cluster in a predetermined micro-space (hereinafter referred to as a "culture space" as appropriate). The culture method is a culture method for forming a cell cluster by culturing a population including at least two types of cells including a cell derived from a stem cell and a mesenchymal cell. The cell derived from a stem cell is at least one cell selected from the group consisting of an endodermal cell, an ectodermal cell, and a mesodermal cell which are derived from a stem cell. The above-mentioned cells are cultured together with at least one cell and/or factor selected from the group consisting of a vascular cell, a factor secreted from a vascular cell, and a factor secreted due to the presence of both a vascular cell and a mesenchymal cell.

Further, in the culture method, the volume of the space (culture space) in which cells are movable is 400 mm$^3$ or less. Furthermore, when the volume of the space in which cells are movable is represented by V mm$^3$ and the number of mesenchymal cells seeded in the space in which cells are movable is represented by N, the N/V ratio is in a range from 35 to 3000.

In other words, the above culture method is a method for obtaining a cell cluster by co-culturing a plurality of cells. Further, the following conditions are satisfied:

the plurality of cells included in a cell suspension include any one of the following (A) to (C);

the culture space has a size of 400 mm$^3$ or less; and when the volume of the culture space is represented by V mm$^3$ and the number of mesenchymal cells present in the space in which cells are movable is represented by N, the N/V ratio is in a range from 35 to 3000.

(A) at least one cell selected from the group consisting of an endodermal cell, an ectodermal cell, and a mesodermal cell, the cell being a cell derived from a stem cell, i.e., a cell derived from a stem cell (hereinafter referred to as a "triploblastic cell derived from a stem cell" as appropriate), (B) a mesenchymal cell, and (C) at least one cell and/or factor (hereinafter referred to as "a vascular cell or a secretor factor" as appropriate) selected from the group consisting of a vascular cell, a factor secreted from a vascular cell, and a factor secreted due to the presence of both a vascular cell and a mesenchymal cell.

Hereinafter, the terms "a cell derived from a stem cell" and "a triploblastic cell derived from a stem cell" are not distinguished from each other, that is, they have the same meaning.

The culture space is a space in which cells to be cultured in the space can freely move. In other words, the culture space is an area in which cells can move three-dimensionally within the area. Since the volume of the culture space is 400 mm$^3$ or less, the cells during culture move within the space specified (limited) by the volume.

The cells move to thereby form an aggregate. The aggregated cells further proliferate and differentiate. The proliferating or differentiating cells form a cell cluster. An aggregate represents a state in which cells are connected to each other. The cells in such a state have not started differentiation or proliferation yet. However, the cells having a high proliferation ability or a high differentiation ability may cause proliferation or differentiation and aggregation in parallel. In the state in which cells aggregate, the cells are dispersed by only applying a physically small shearing strength, for example, by gently agitating the medium. The specification of the size of the culture space will be described later with reference to FIG. 7 and the like.

Additionally, the size of the culture space is preferably determined in consideration of the size of a cell cluster of interest. This is based on the following findings.

According to the findings of the present inventors, the important factors for preparing a cell cluster which has functions similar to those in vivo and does not differentiate into a tissue of an organ other than a transplantation target are as follows:

the ratio of mesenchymal cells present in the medium of the culture space; and the limitation of an area in which mesenchymal cells are movable.

Explanation of a Cell Cluster

A cell cluster according to an embodiment is a cell group obtained by co-culturing a triploblastic cell derived from a stem cell, a mesenchymal cell, and a vascular cell or a secretor factor. The "triploblastic cell derived from a stem cell" and the "vascular cell or secretor factor" described herein are included in the above-mentioned cell suspension. The "triploblastic cell derived from a stem cell" and the "vascular cell or secretor factor" are respectively described in the above items (A) and (C).

Additionally, the cell cluster is based on the premise that the cell cluster has a plurality of functions which are included in a tissue of interest. However, the cell cluster may or may not be differentiated to the same level as a biological tissue. The cell cluster may or may not be formed of mature cells.

As for the expression of a plurality of functions in a cell cluster, they are expressed as follows. A plurality of functions included in a cell cluster are preferably similar to the functions included in a cell or a biological tissue sampled from a fetus. These functions can be specified as, for example, gene expression patterns.

A plurality of functions included in a cell cluster are preferably similar to the functions included in a cell sampled from an adult, or a biological tissue sampled from an adult. A plurality of functions included in a cell cluster are preferably similar to the above-mentioned plurality of functions, rather than to a plurality of functions included in a stem cell or a triploblastic cell derived from a stem cell.

At lease two types (preferably, three types) of cells are co-cultured. Thus, the cells are aggregated. Further, the aggregated cells are caused to differentiate or proliferate, or are caused to differentiate and proliferate in parallel to thereby form a cell cluster.

In addition, the shape of the cell cluster used herein is not limited to a spheroid shape. The cell cluster used herein may have any shape, as long as the cell cluster is a mass of a plurality of cells.

The term "spheroid" refers to a spherical cell cluster formed by aggregating a number of cells. The spheroid is a state in which cells are aggregated in a three-dimensional state.

The following terms are used in this specification.

The term "biological tissue" refers to a unit of a structure including several specific types of cells which aggregate in a predetermined pattern. The biological tissue has a unified role as a whole. For example, each organ in a living body is formed by several types of tissues which aggregate in a predetermined pattern. A cell cluster (cell group) which is formed of differentiated cells and has an arbitrary function is herein referred to as a tissue.

The term "an endodermal, ectodermal, or mesodermal cell derived from a stem cell" (hereinafter referred to as "a triploblastic cell derived from a stem cell") will be explained below.

The term "stem cell" refers to a cell which includes a cell selected from the group consisting of a fetal stem cell, an embryonic stem cell (ES cell), and an induced pluripotent stem cell (iPS cell). The stem cell has infinite proliferative potential. In this specification, the stem cell may be a cell capable of differentiating into any one of an endodermal organ, a mesodermal organ, and an ectodermal organ.

The term "endodermal cell" refers to a cell capable of differentiating into a mesodermal organ, such as a liver, pancreas, intestinal tract, lung, thyroid, parathyroid, or urinary tract.

The term "ectodermal cell" refers to a cell capable of differentiating into an ectodermal organ such as a brain, spinal cord, adrenal medulla, epidermis, hair/nail/dermal-gland, sensory organ, peripheral nerve, or lens.

The term "mesodermal cell" refers to a cell capable of differentiating into a mesodermal organ such as a kidney, ureter, heart, blood, gonad, adrenal cortex, muscle, skeleton, dermis, connective tissue, or mesothelium.

That is, the term "a triploblastic cell derived from a stem cell" refers to a cell having the characteristics of an endodermal organ, an ectodermal organ, or a mesodermal organ derived from a cell selected from the group consisting of an ES cell and an iPS cell.

Whether a cell is one which can differentiate into an endodermal organ, an ectodermal organ, or a mesodermal organ can be confirmed by examining the expression of marker proteins. For example, if any one or a plurality of predetermined marker proteins are expressed, the cell can be judged to be a cell that can differentiate into an endodermal organ.

For example, a cell which can differentiate into a liver can discriminate HHEX, SOX2, HNF4A, AFP, ALB, and the like as markers. PDX1, SOX17, SOX9, and the like are markers for a cell which can differentiate into a pancreas. CDX2, SOX9, and the like are markers for a cell which can differentiate into an intestinal tract. SIX2, SALL1, and the like are markers for a cell which can differentiate into a kidney. NKX2-5 MYH6, ACTN2, MYL7, HPPA, and the like are markers for a cell which can differentiate into a heart. C-KIT, SCA1, TER119, HOXB4, and the like are markers for a cell which can differentiate into blood. HNK1, AP2, NESTIN, and the like are markers for a cell which can differentiate into a brain or spinal cord.

The term "mesenchymal cell" refers to a cell in a connective tissue which is mainly derived from mesoderm. The mesenchymal cell is a cell for forming a structure for supporting a cell that functions in a biological tissue. The mesenchymal cell is a connective tissue cell.

An undifferentiated mesenchymal cell includes a cell that is destined to differentiate into a mesenchymal cell but has not yet differentiated into a mesenchymal cell. The mesenchymal cell used in the present invention may be a differentiated one or an undifferentiated one. The undifferentiated mesenchymal cell is also referred to as a mesenchymal stem cell.

Whether a cell is an undifferentiated mesenchymal stem cell or not can be confirmed by examining the expression of marker proteins. Examples of the marker proteins include Stro-1, CD29, CD44, CD73, CD90, CD105, CD133, CD271, and Nestin.

If any one or a plurality of the marker proteins are expressed in a cell, the cell can be judged to be an undifferentiated mesenchymal cell. The mesenchymal cell in which all the markers described above are not expressed can be judged to be a differentiated mesenchymal cell.

Among the terms used by those skilled in the art to describe the mesenchymal cell, the following ones are used in the present invention: mesenchymal stem cells, mesenchymal progenitor cells, mesenchymal cells (R. Peters, et al. PLoS One. 30; 5 (12): e15689. (2010)), and so on.

In the present invention, the mesenchymal cell derived from a human is mainly used. In the present invention, for example, an undifferentiated mesenchymal cell derived from a non-human animal, such as a mouse, a rat, a dog, a pig, or a monkey, may also be used.

The term "vascular cell" refers to a cell that constitutes a vascular endothelium, or a cell which can differentiate into such a cell. The term "vascular cell" described herein refers to a vascular cell included in the above-mentioned item (C). The vascular cell is a cell other than a factor secreted from a vascular cell and the like. The term "vascular cell" does not have any meaning other than a vascular cell.

Whether a cell is a vascular cell or not can be confirmed by examining the expression of marker proteins such as TIE2, VEGFR-1, VEGFR-2, VEGFR-3, and CD41. If any one or a plurality of the marker proteins are expressed, the cell can be judged to be a vascular cell.

The vascular cell used in the present invention may be a differentiated vascular cell or an undifferentiated vascular cell. It can be confirmed whether the vascular cell is a differentiated cell or not by the expression of marker proteins CD31 and CD144.

Among the terms used by those skilled in the art to describe the vascular cell, the following ones are used in the present invention: endothelial cells, umbilical vein endothelial cells, endothelial progenitor cells, endothelial precursor cells, vasculogenic progenitors, hemangioblast (H J. joo, et al. Blood. 25; 118 (8): 2094-104. (2011)), and so on.

When a vascular cell is used in the present invention, a vascular cell derived from a human is mainly used. In the present invention, a vascular cell derived from a non-human animal, such as, a mouse, a rat, a dog, a pig, or a monkey, may also be used.

The term "organ bud" refers to a structure which can differentiate into an organ as a result of maturing. The organ bud is a structure including three types of cells. The three types of cells are a triploblastic cell derived from a stem cell, a vascular cell, and an undifferentiated mesenchymal cell, or a cell differentiated from those cells.

Whether or not a certain structure is an organ bud can be confirmed by, for example, performing at least one of the following methods. One of the methods is that the structure is transplanted into a living body to check if the structure is capable of differentiating into an organ of interest. In this case, if the structure differentiates into an organ of interest, it can be determined that the structure is an organ bud. The other one of the methods is to check if the structure includes all the above-mentioned three types of cells. If the structure includes all the three types of cells, it can be determined that the structure is an organ bud.

The organ bud may be one which differentiates into an organ such as a kidney, heart, lung, spleen, esophagus, stomach, thyroid, parathyroid, thymus, gonad, brain, or spinal cord. As the organ bud, an organ bud that differentiates into an endodermal organ is preferable. Examples of the organ bud include an organ bud (liver bud) which differentiates into a liver, an organ bud (pancreatic bud) which differentiates into a pancreas, and an organ bud which differentiates into an intestinal tract.

Whether or not a certain structure is an organ bud which differentiates into an endodermal organ can be confirmed by checking the expression of proteins serving as a marker in the structure. If one or more of the marker proteins described later are expressed in the structure, it can be determined that the structure is an organ bud which differentiates into an endodermal organ.

For example, HHEX, SOX2, HNF4A, AFP, ALB, and the like are markers for a liver bud. PDX1, SOX17, SOX9, and the like are markers for a pancreatic bud. CDX2, SOX9, and the like are markers for an organ bud which differentiates into an intestinal tract.

Among the terms used by those skilled in the art to describe the organ bud, the following ones are used in the present invention: a liver bud, liver diverticula, liver organoid, pancreatic (dorsal or ventral) buds, pancreatic diverticula, pancreatic organoid, intestinal bud, intestinal diverticula, intestinal organoid (K. Matsumoto, et al. Science. 19; 294 (5542):559-63. (2001)), and so on.

The term "fetus" refers to a fetus which develops from a fertilized egg. The fetus communicates with its mother's body in some way. The fetus grows based on nutrients from the mother's body, and is to be born after it is fully grown. The term "a cell sampled from a fetus" refers to a cell sampled from the fetus. For example, a cell sampled from a fetus includes a biological tissue of a fetal liver and commercially-available fetal hepatocytes.

The term "a cell sampled from an adult" refers to a cell sampled from a living body which has fully grown and is reproductive. A cell sampled from an adult includes, for example, commercially-available human primary hepatocytes and biopsied biological tissues.

As "a cell or a biological tissue sampled from an adult", cells derived from a human or an animal are available from manufacturers. Hepatocytes are available from Charles River Laboratories International, Inc. and KAC Co., Ltd.

The above-mentioned cell or biological tissue can also be sampled from an animal. Examples of a method for sampling a hepatocyte from a rat or a mouse include a method of separating a hepatocyte by a two-step collagenase perfusion method. The following method, for example, can be used for a rat. First, a cannula is inserted into the portal vein of the rat. Next, its blood is removed using a phosphate buffer (pre-perfusate) heated to 37 degrees. Then, the collagen of the tissue is dissolved with a Collagenase solution heated to 37 degrees. This method enables only the cells to be recovered.

"A cell or biological tissue sampled from a fetus" is commercially available. The cell or tissue is available from a cell bank or the like. For example, the cell or biological tissue is available from VERITAS Corporation.

Explanation of a Plurality of Functions

The term "a plurality of functions" refers to functions which can be included in a cell cluster. In other words, the plurality of functions are functions which can be detected depending on the maturation stage of a cell cluster. In one embodiment, functions which can be measured by the gene expression level and the amount of protein can be used as the plurality of functions. The cell cluster used herein may or may not include a plurality of functions. Accordingly, the description of the plurality of functions is omitted.

The term "co-culture" generally refers to culture of two or more different types of cells together after mixing the cells.

The co-culture according to an embodiment includes the steps of: forming a cell cluster from the above-mentioned cells; further culturing the cell cluster to allow the cell cluster to proliferate and differentiate; and further culturing the cell cluster and allowing the cell cluster to be mature.

For example, after the above-mentioned cells form an organ bud, which is one form of the cell cluster, the organ bud is cultured to thereby allow the organ bud to be mature. An example in which after the cells are caused to form a cell cluster, the cell cluster is caused to form an organ bud and the organ bud is allowed to be mature is described herein to facilitate the explanation. However, as described above, the differentiated cells are not limited to an organ bud. Examples of the differentiated cells include a cell and a tissue which are formed by differentiating a cell cluster.

The co-culture described blow includes: (1) a step of causing cells to form a cell cluster; (2) a step of causing the cell cluster to form an organ bud; and (3) a step of culturing the organ bud and allowing the organ bud to mature.

The steps will be described below.

(1) Step of Causing Cells to form a Cell Cluster (Cell Cluster Forming Step)

Three types of cells, i.e., a triploblastic cell derived from a stem cell, a mesenchymal cell, and a vascular cell or a secretor factor are co-cultured, to thereby cause these cells to form a cell cluster (for several hours to 1 day).

(2) Step of Causing the Cell Cluster to Form an Organ Bud (Organ Bud Forming Step)

The cell cluster is further cultured. The cells of the cell cluster are caused to proliferate and differentiate, to thereby allow the cell cluster to form an organ bud.

(3) Step of Allowing the Organ Bud to Mature (Maturation Step)

The above-mentioned organ bud shows a state in which the proliferation rate of the cells decreases, or the cells do not proliferate. In this state, the state in which the proliferation rate of the cells decreases, or the cells do not proliferate is maintained for a predetermined period. During this period, the culture is continuously performed.

The triploblastic cell derived from a stem cell may be derived from any type of cell or tissue. The triploblastic cell derived from a stem cell is preferably obtained by using a fetal stem cell derived from an induced pluripotent stem cell or an embryo prepared using a reprogramming technique.

As methods for forming a cell cluster, various methods are known, such as a hanging drop method in which a cell cluster is formed in a droplet; a method using a chamber having a concave and convex pattern of a mesh structure or a nano-order pillar structure on the bottom surface of the culture chamber; a method of forming a cell cluster in a state where cells are suspended in a medium while agitating the medium in a roller bottle; a method of culturing cells on a gel such as agarose or matrigel; and a method of forming a cell cluster by using a culture chamber which is subjected to a cell non-adhesive treatment and is placed in a stationary state. A cell cluster may be formed by any one of these methods. A cell cluster may be formed by a combination of these methods. Various specific methods are introduced in various documents and are described in, for example, the following documents.

Francesco Pampaloni, et. al., "The third dimension bridges the gap between cell culture and live tissue", Nature reviews molecular cell biology volume 8, October 2007, pp. 839-845

Markus Rimann, et. al., "Synthetic 3D multicellular systems for drug development" Current Opinion in Biotechnology 2012 23, 2012, pp. 1-7

In the cell cluster forming step, the group consisting of an endodermal cell, an ectodermal cell, and a mesodermal cell is used. The endodermal cell, the ectodermal cell, and the mesodermal cell are derived from a stem cell. The endodermal cell, the ectodermal cell, or the mesodermal cell preferably includes a cell selected from cells derived from a fetal stem cell or an induced pluripotent stem cell.

Additionally, the group consisting of an endodermal cell, an ectodermal cell, and a mesodermal cell preferably includes a cell that is derived from an induced pluripotent stem cell and is capable of differentiating into an endodermal cell. This is because the level of required ethical standards is low. Further, since the homogeneity due to the establishment of standard strains by using a cell derived from an induced pluripotent stem cell can be secured, it is preferable to use a cell derived from an induced pluripotent stem cell.

The ratio of the number of three types of cells in co-culture is not particularly limited as long as an organ bud can be formed. The suitable ratio of the number of the cells is (triploblastic cells derived from a stem cell):(vascular cells):(mesenchymal cells)=10:10 to 5:0.1 to 1.

The following materials are illustrated as a factor secreted from a vascular cell, a factor secreted from a mesenchymal cell, and a factor secreted due to the presence of both a vascular cell and a mesenchymal cell. The materials are FGF2, FGF5, BMF4, BMP6, CTGF, and the like. The above-mentioned factors are not limited to these examples.

The amount of addition of these materials is as follows. The appropriate amount of addition of FGF2 is in a range from 10 to 100 ng/ml per $1 \times 10^6$ cells, and is preferably about 20 ng/ml. The appropriate amount of addition of BMF4 is in a range from 10 to 100 ng/ml per $1 \times 10^6$ cells, and is preferably about 20 ng/ml.

Any medium can be used during culture as long as a cell cluster having a plurality of predetermined functions is formed. The plurality of predetermined functions are a plurality of functions similar to a plurality of functions included in a cell of a living body or a biological tissue. The cell of a living body is a cell sampled from a fetus or a living body. The biological tissue is a biological tissue sampled from a fetus or a living body. Whether the plurality of functions of the cell cluster are similar to the plurality of functions of the biological tissue or the like may be confirmed by gene expression patterns.

It is preferable to use a medium for culture. It is preferable to use a medium for culturing a stem cell. As the medium for culturing a stem cell, a medium for culturing an ES cell or an iPS cell is preferable. It is preferable to use, for example, a medium obtained by mixing these media.

As a medium for culturing a vascular cell, any medium may be used. However, preferably, a medium containing at least one of the following substances may be used: hEGF (recombinant human epidermal growth factor), VEGF (vascular endothelial growth factor), hydrocortisone, bFGF, ascorbic acid, IGF1, FBS, antibiotics (e.g., gentamycin or amphotericin B), heparin, L-glutamine, phenolred, and BBE.

As the medium for culturing a vascular cell, EGM-2 BulletKit (manufactured by Lonza, Inc.), EGM BulletKit (manufactured by Lonza, Inc.), VascuLife EnGS Comp Kit (manufactured by LCT, Inc.), Human Endothelial-SFM Basal Growth Medium (manufactured by Invitrogen, Inc.), human microvascular endothelial cell proliferation medium (manufactured by TOYOBO CO., LTD.), and the like can be used.

Any medium can be used as the medium for culturing a triploblastic cell derived from a stem cell. When an artificial tissue of interest is a liver tissue, it is preferable to use a medium for culturing a hepatocyte. A medium containing at least one species of an ascorbic acid, BSA-FAF, insulin, hydrocortisone, and GA-1000 is preferable. A medium obtained by removing hEGF (recombinant human epidermal growth factor) from HCM BulletKit (manufactured by Lonza, Inc.) which is commercially available as a medium for culturing a hepatocyte is preferable. A medium obtained by adding 1% of B27 Supplements (manufactured by GIBCO CO., LTD.) and 10 ng/mL of hHGF (manufactured by Sigma-Aldrich Co.) to RPMI1640 (manufactured by Sigma-Aldrich Co.) is preferable.

More preferably, a medium obtained by adding Dexamethasone, Oncostatin M, and HGF to a medium obtained by removing hEGF (recombinant human epidermal growth factor) from a mixture of GM BulletKit (manufactured by Lonza, Inc.) and HCM BulletKit (manufactured by Lonza, Inc.) at a ratio of 1:1 is used.

The temperature during culture is not particularly limited, but is preferably 30 to 40° C., and more preferably 37° C.

The period of culture is not particularly limited, but is preferably 3 to 50 days, and more preferably 15 days.

Culture chambers used for the cell cluster forming step may be different from those for the maturation step. The cell cluster forming step is a step of forming a cell cluster as a nucleus. The maturation step is a step of allowing the cell cluster to mature until the cell cluster has a plurality of predetermined functions. The plurality of predetermined functions are a plurality of functions similar to a plurality of functions included in a cell sampled from a fetus, or a biological tissue sampled from a fetus. Alternatively, the plurality of predetermined functions are a plurality of functions similar to a plurality of functions included in a cell sampled from an adult, or a biological tissue sampled from an adult.

Culture chambers may be used in all the steps. The hanging drop method may be used in the cell cluster forming step and the maturation step. In this case, cells may be cultured using droplets instead of the culture chambers.

It is preferable that the cells be connected to form an aggregate in the cell cluster forming step and the maturation step. It is also preferable that the cell cluster formed in the cell cluster forming step and the maturation step be a spherical mass formed of connected cells.

Furthermore, the diameter of the cell cluster formed by the cells is preferably in a range from 20 µm to 2 mm, and more preferably in a range from 50 µm to 2 mm. The size of the cell cluster is more preferably in a range from 50 µm to 200 µm. In this case, nutrients (vitamin, amino acid, etc.) and oxygen contained in the medium can be supplied to a central portion of the cell cluster. This makes it possible to prevent necrosis of cells at the central portion of the cell cluster (Efrem Curcio et al., "Mass transfer and metabolic reactions in hepatocyte spheroids cultured in rotating wall gas-permeable membrane system", Biomaterials 28 (2007) 5487-5497).

Regarding a Culture Chamber

A culture chamber having the following structure, for example, is used.

FIG. 1 is a diagram showing an example of a culture chamber according to an embodiment. FIG. 1 shows a part of a culture plate 3 including a plurality of culture chambers 1. The upper part of FIG. 1 shows some of a plurality of recesses 10 which are formed in the bottom of each of the culture chambers 1, when viewed from the top of the culture plate 3. The plurality of recesses 10 are arranged in each of the culture chambers 1. In terms of the production of the culture chambers 1 and the efficiency of cell culture, it is preferable to arrange the plurality of recesses 10 in a regular manner. One culture chamber 1 corresponds to, for example, one well of a plate including a plurality of wells. In other words, the plurality of recesses 10 are arranged in the respective wells of a well plate.

A well plate is an experimental/testing instrument formed of a flat plate having a number of dents (holes or wells). Each well of the well plate is used as a test tube or a petri dish. The number of wells is, for example, 6, 24, 96, 384, or more.

The bottom of each well may be flat or round. Examples of the well plate include a deep well plate. The deep well plate is a well plate composed of a combination of a number of long microtubes.

Figure 2:
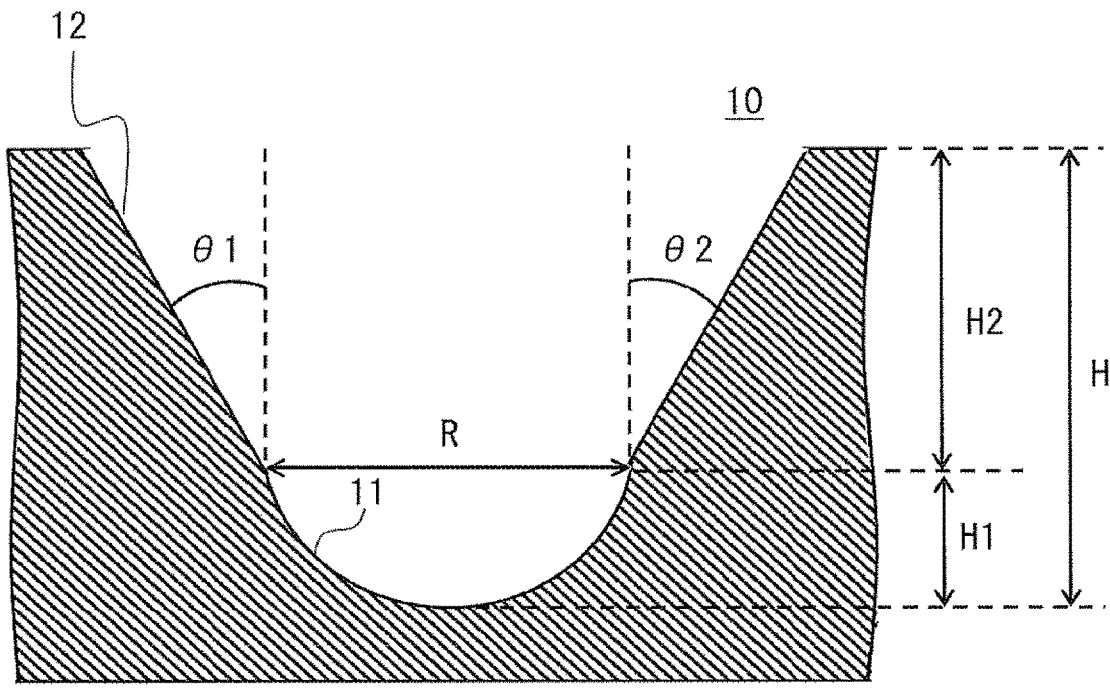
FIG. 2 is a sectional view showing an example of the shape of a recess according to the embodiment when viewed from a lateral direction.
Figure 3:
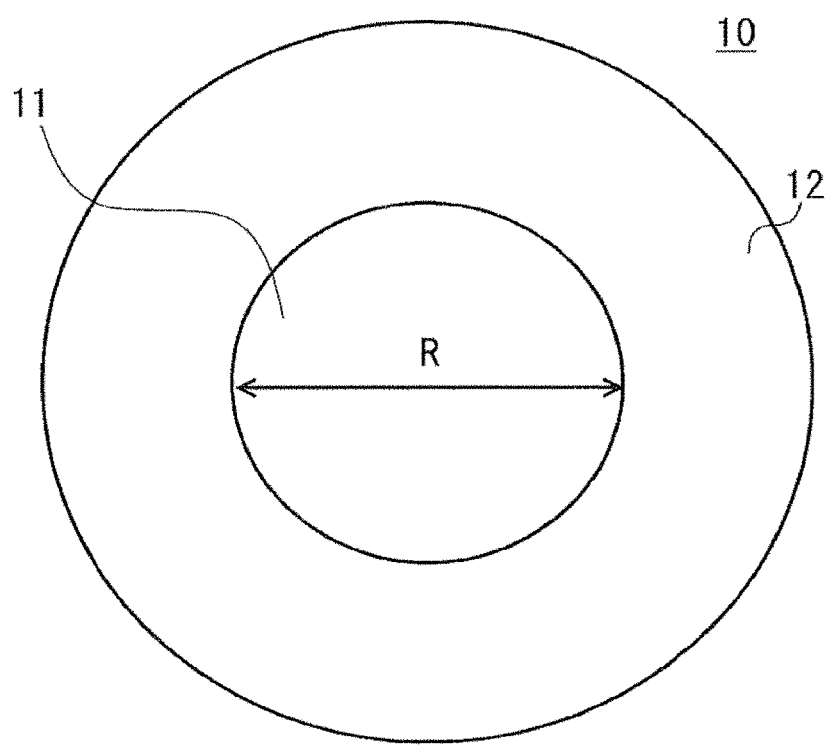
FIG. 3 is a diagram showing an example of the shape of the recess according to the embodiment when viewed from above.

FIGS. 2 and 3 are diagrams showing an example of the shape of each recess according to a first embodiment. FIG. 2 shows a sectional view of one recess 10 when viewed from a lateral direction, and FIG. 3 a diagram showing one recess 10 when viewed from above.

Each recess 10 is composed of a bottom portion 11 and an opening 12. The opening 12 is a horn portion having a horn shape. An upper end of the opening 12 has an opening. The bottom portion 11 is a portion corresponding to the bottom of the culture chamber 1, and the opening 12 is a portion disposed above the bottom portion 11. A portion where the bottom portion 11 and the opening 12 are in contact is referred to as a boundary. In FIG. 2, a portion whose length is indicated by an arrow R corresponds to the location of the boundary. In FIG. 3, the boundary location is indicated by a double dotted-dashed line. Note that the bottom portion 11 and the opening 12 are formed of a continuous surface and are produced in an integrated manner.

FIGS. 2 and 3 show an equivalent diameter R and a depth (height) H of each of the plurality of recesses 10 formed in the culture chamber 1.

The term "equivalent diameter R" refers to the diameter of a circle inscribed in the bottom portion 11 of each recess 10. In this case, the equivalent diameter R is the diameter of an inscribed circle that is inscribed at the boundary between the bottom portion 11 and the opening 12. More specifically, the equivalent diameter R is the diameter of a circle inscribed in a shape of a plane that is perpendicular to the direction of the height H of each recess 10 at the boundary.

The term "depth H" refers to a length from the bottom on the inside of the bottom portion 11 to an upper end of each recess 10. The upper end of the recess 10 corresponds to an end (upper end) of the opening 12. The depth H corresponds to the depth of a space formed by the recess 10. In other words, the depth H is a depth from the bottom of a space, which is formed by the bottom portion 11, to an upper end of a space formed by the opening 12. FIG. 2 shows not only the depth H of the recess 10, but also a depth H1 of the bottom portion 11 and a depth H2 of the opening 12.

The bottom portion 11 forms a space (first space) in which cells are cultured. The bottom portion 11 has, for example, a hemispherical shape. For example, a shape obtained by dividing a spherical shape having the equivalent diameter R as a diameter into halves can be used. The shape of the bottom portion 11 is not limited to a hemispherical shape.

The opening 12 forms a space (second space) that operates to support culture and collection of cells. The opening 12 is formed of a wall which surrounds an area from a boundary between the opening 12 and the bottom portion 11 to an end (tip) of the recess 10 and which has a taper angle in a range from 1 degree to 20 degrees. The taper angle of the wall constituting the opening 12 is preferably in a range from 5 degrees to 15 degrees, and more preferably 10 degrees. This is because if the taper angle is extremely small, it is difficult to transfer cells from the recesses into the medium during collection of the cells, and if the taper angle is extremely large, the cells are removed during replacement of the medium.

Taper angles are represented by θ1 and θ2 in FIG. 2. In an example of the shape of each recess 10 shown in FIGS. 2 and 3, the taper angles θ1 and θ2 are substantially the same.

The boundary between the bottom portion 11 and the opening 12 is formed in such a manner that the equivalent diameter R is in a range from 50 μm to 1 mm. To supply nutrients to a central portion of a cell cluster, the equivalent diameter is preferably in a range from 50 μm to 500 μm, and more preferably in a range from 100 μm to 500 μm.

Additionally, the depth H from the bottom of the bottom portion to the end is set to be in a range from 0.5 to 3 times the equivalent diameter R. The depth H is preferably in a range from 0.7 to 1.2 times the equivalent diameter R, and more preferably in a range from 0.8 times to 1 time the equivalent diameter R.

In the culture chamber, the area between two adjacent recesses 10 is preferably flat. For example, the distance between two recesses 10 is preferably in a range from 5 μm to 50 μm. This is for the purpose of preventing cells from running on the wall. This structure provides an effect of preventing cells from adhering onto the wall and proliferating to form a cell cluster on the wall. However, if the wall is thin, cracking is more likely to occur due to a vibration during cell seeding or replacement of the medium. Accordingly, it is preferable that the thickness of the wall be 5 μm or more. In view of this, it is preferable that the thickness of the wall is in a range from 5 to 20 μm.

Each culture chamber 1 has a shape as described above and is preferably produced as follows.

The culture chamber 1 is preferably a resin molding formed of one or a combination of two or more selected from the group consisting of acrylic resin, polylactic acid, polyglycolic acid, styrene resin, acrylic styrene copolymer resin, polycarbonate resin, polyester resin, polyvinyl alcohol resin, ethylene vinyl alcohol copolymer resin, thermoplastic elastomer, vinyl chloride resin, and silicon resin.

It is preferable to perform a treatment on each recess 10 so that the water contact angle on each recess 10 included in the culture chamber 1 becomes 45 degrees or less. As the treatment, a treatment for forming a functional group by a surface modification treatment method is preferable. The surface modification treatment method is preferably one of plasma treatment, glass coating, corona discharge, and UV ozonation, or a combination thereof.

Additionally, it is preferable that a hydrophilic polymer chain that inhibits cell adhesion be immobilized on each recess 10. More preferably, a hydrophilic polymer chain is immobilized on the surface of each recess 10 that is treated so that the water contact angle becomes 45 degrees or less as mentioned above.

Furthermore, it is preferable that a phospholipid or a phospholipid-polymer complex be immobilized on the surface of each recess 10. More preferably, this immobilization treatment is performed on each recess 10 that is treated so that the water contact angle becomes 45 degrees or less. More preferably, the immobilization treatment is performed on each recess 10 on which a hydrophilic polymer chain is immobilized. More preferably, the immobilization treatment is performed on each recess 10 on which a combination of the above-mentioned treatment and the immobilization is carried out.

Each recess 10 preferably has a cell non-adhesive surface which is obtained by immobilizing a polymer on the surface treated so that the water contact angle becomes 45 degrees or less. To obtain a water contact angle of 45 degrees or less, it is preferable to form a functional group in each recess 10. The functional group is preferably formed by the surface modification treatment method. The surface modification treatment method is preferably one of plasma treatment, glass coating, corona discharge, and UV ozonation, or a combination thereof. As the polymer, a polymer selected from a hydrophilic polymer chain that inhibits cell adhesion, a phospholipid, and a phospholipid-polymer complex is preferable. This treatment is preferably carried out together with each of the above-mentioned treatments, or a combination of the above-mentioned treatments.

Poly(hydroxyethyl methacrylate) is preferably used as the above-mentioned hydrophilic polymer chain. More preferably, the average molecular weight of poly(hydroxyethyl methacrylate) is 100,000 or more.

Figure 4:
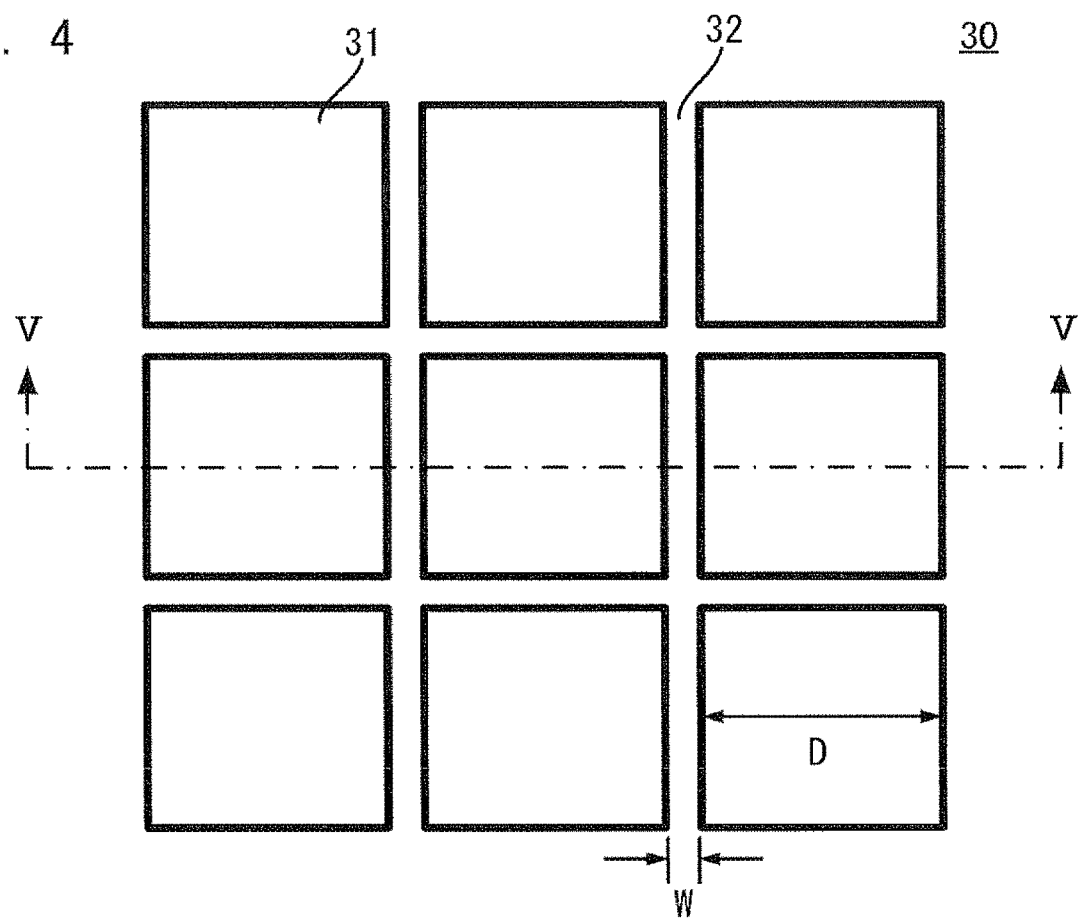
FIG. 4 is a diagram showing another example of the shape of the culture chamber.
Figure 5:
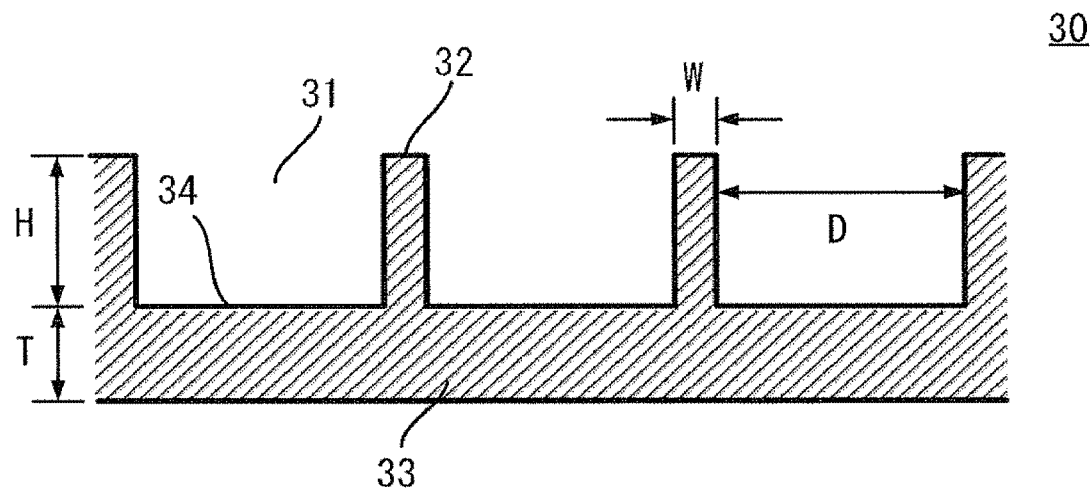
FIG. 5 is a cross-sectional view of the culture chamber shown in FIG. 4 taken along a line V-V.

As the culture chamber 1, not only the culture chambers shown in FIGS. 1 to 3, but also culture chambers in which micropatterns shown in FIGS. 4 and 5 are formed can be used.

FIG. 4 shows another example of the shape of the culture chamber used in an embodiment. FIG. 5 is a sectional view of the culture chamber taken along a line V-V shown in FIG. 4.

A culture chamber 30 includes culture spaces 31, walls 32, and a bottom portion 33.

Each culture space 31 is an area partitioned by the walls 32 and the bottom portion 33. The culture space 31 serves as a three-dimensional space area (culture area) in which cells are cultured. The culture space 31 is also referred to simply as "space" or "micro-space".

The walls 32 are partition walls that partition the culture spaces 31. It can also be said that each of the walls 32 is a convex portion that forms a concave and convex pattern in the culture chamber 30.

The bottom portion 33 functions as a substrate for the culture chamber 30. The surface of the bottom portion 33 on which the culture space 31 is formed is a part of the culture area (culture surface). The bottom portion 33 has the same area as that of the bottom portion of each well formed in the culture plate shown in FIG. 1, for example. The bottom portion of each well is used as the bottom portion 33. The bottom portion 33 forms the bottom of each culture space 31. The surface of the bottom portion 33 that is a part of the surface forming the culture space 31 and serves as the culture area is referred to as "a bottom culture surface 34".

As for each culture space 31 formed in the culture chamber 30, FIGS. 4 and 5 show an equivalent diameter D, the height (depth) H, a width (thickness) W of each of the walls 32, and a thickness T of the bottom portion 33. FIGS. 4 and 5 show a case where the bottom portion 33 is produced integrally with the walls 32.

The equivalent diameter D is similar to the equivalent diameter R shown in FIG. 2. The term "equivalent diameter D" refers to the diameter of an inscribed circuit that is inscribed in the culture space 31, more specifically, the shape of a surface parallel to the bottom portion 33 of the culture space 31 (the shape of the front surface). In other words, the equivalent diameter D refers to the diameter of an inscribed circuit having a shape of a surface perpendicular to the direction of the height H of the culture space 31. In this case, the shape of the culture space 31 as viewed from the front side may vary depending on the height H. In this case, a maximum value of the width of the space area in which an established hepatic cell line is cultured is defined as the equivalent diameter.

The height H is the length from the bottom (bottom culture surface 34) of the culture space 31 to the upper surface of each wall 32. It can also be said that the height H is the depth of each culture space 31. When the bottom culture surface 34 is a flat surface, the height H is the same as the height of each wall 32.

The width W of each wall 32 is the thickness of each wall 32. It can also be said that the width W is the distance between two adjacent culture spaces 31.

In the culture chamber 30 (in other words, in each well), the plurality of culture spaces 31 are arranged in an array as shown in FIG. 4. The number or size of the culture spaces 31 included in the culture chamber 30 depend on the number of wells (the size of wells), which are formed in the culture plate, and on the size of each of the culture spaces 31 and the walls 32. FIGS. 4 and 5 show nine culture spaces 31. These are illustrated for ease of explanation, and thus the number of culture spaces 31 does not correspond to the actual number of culture spaces 31 included in the culture chamber 30 (each well).

Figure 6:
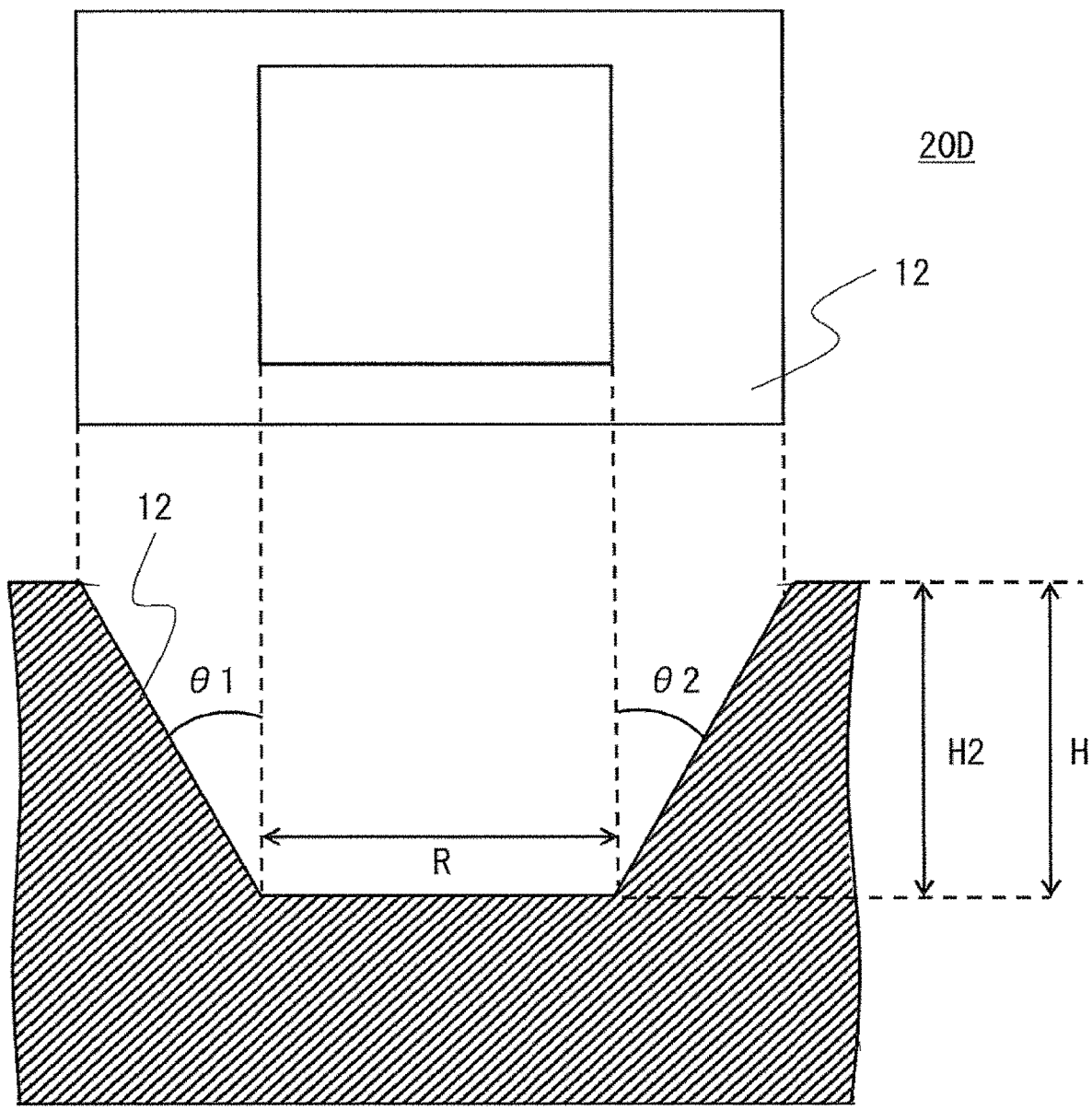
FIG. 6 is a diagram showing a further example of the shape of the culture chamber.

A recess 20D shown in FIG. 6 may also be used as a culture chamber. FIG. 6 shows an example of the shape of the recess 20D having a linear bottom portion, in other words, a bottom portion that provides no space. The upper part of FIG. 6 shows an elevational view of the recess 20D as viewed from the top, and the lower part of FIG. 6 shows a sectional view of the recess 20D. The recess 20D is formed of the opening 12.

Figure 7:
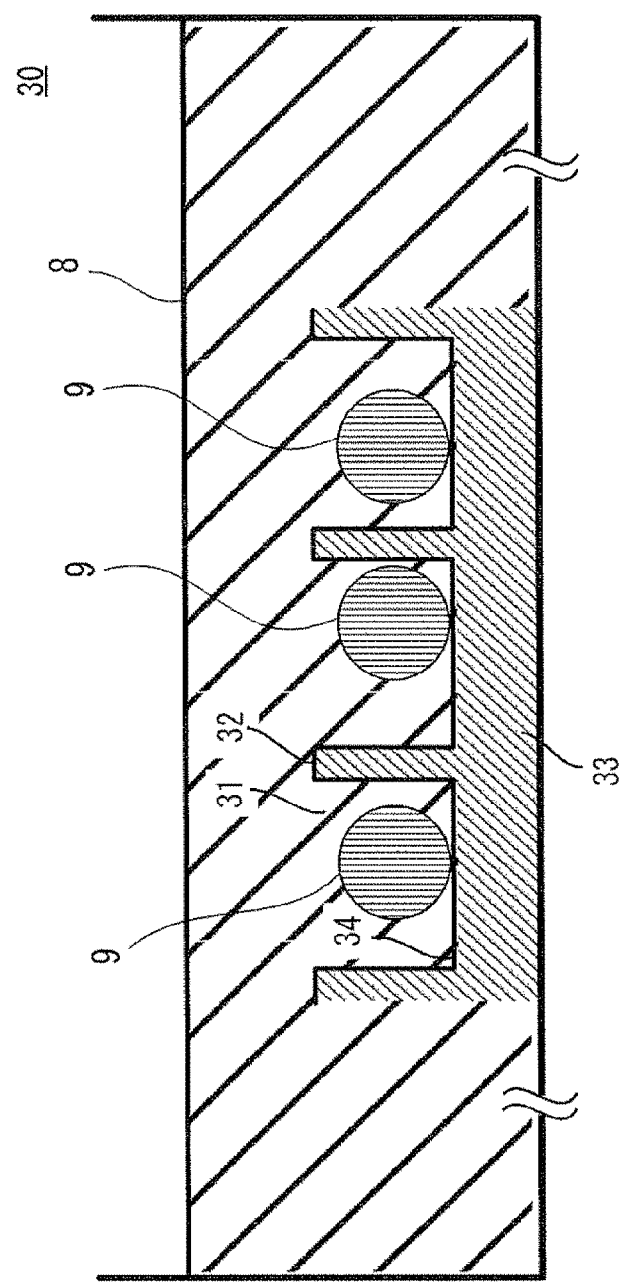
FIG. 7 is a diagram showing an example of a state in which cells are cultured using the culture chambers shown in FIGS. 4 and 5.

FIG. 7 shows an example of a state in which cells are cultured using the culture chamber shown in FIGS. 4 and 5. FIG. 7 shows one culture chamber 30 corresponding to one well of a well plate. FIG. 7 also shows three culture spaces 31 among the plurality of culture spaces 31 formed in the culture chamber 30. In FIG. 7, the illustration of the other culture spaces 31 is omitted. A medium 8 is injected into the culture chamber 30 so that the plurality of culture spaces 31 are filled with the medium. The figure shows a state in which a cell cluster 9 is formed in each culture space 31.

In this embodiment, the volume of the space in which cells are movable corresponds to the volume (V $mm^3$) of each culture space 31. Specifically, the volume of each culture space 31 shown in FIGS. 4 and 5 is the product of the height H and the area of the bottom culture surface 34. Note that the cells during culture are based on the premise that the cells do not move across the walls 32 of the culture space 31.

In this embodiment, the volume V $mm^3$ of the culture space is equal to or less than 400 $mm^3$. Additionally, when the number of mesenchymal cells seeded in the culture space is represented by N, the cell number N of the cells is adjusted so that the N/V ratio is in a range from 35 to 3000. When the volume of the culture space is limited, the range in which the cells are movable is also limited. Further, when the number of mesenchymal cells for the volume of the culture space is specified, the density of the mesenchymal cells in the culture space is specified. The present inventors have found that when the conditions for these two elements are satisfied, cultured cells form a cell cluster even if the number of the mesenchymal cells is reduced. The present inventors have also found that the formed cell cluster has functions similar to those in vivo. Furthermore, the present inventors have found that the cell cluster is a safe cell cluster which does not differentiate into a tissue of an organ other than the transplantation target.

The present inventors have found that it is particularly preferable that the ratio of the number of mesenchymal cells present in the space in which the cells are movable to the total number of cells used for culture is preferably 0.5% or more but less than 5%. In this case, the total number of cells used for culture corresponds to the total number of cells derived from a stem cell, mesenchymal cells, vascular cells, and the other cells, and factors are not counted as the number of cells.

In addition, the present inventors have found that when the above-mentioned cells are mixed and co-cultured, the ratio X:Y, which is the ratio of the total cell number (X) of endodermal cells, ectodermal cells, and mesodermal cells, which are derived from a stem cell, to the cell number (Y) of mesenchymal cells, is preferably in a range from 20:1 to 100:1.

The present inventors have also found that a cell cluster is suitably formed when the ratio of the number of mesenchymal cells present in the space in which the cells are movable to the total number of cells used for culture is 0.5% or more. Further, when the above-mentioned cells are mixed and co-cultured and the ratio X:Y, which is the ratio of the cell number (X) of cells derived from a stem cell (triploblastic cells derived from a stem cell) to the cell number (Y) of mesenchymal cells, is in a range from 20:1 to 100:1, an organ bud is suitably formed.

The cell number (X) of cells derived from a stem cell (triploblastic cells derived from a stem cell) is the total number of cells selected from an endodermal cell, an ectodermal cell, and a mesodermal cell, which are derived from a stem cell, or a combination thereof. In other words, the cell number (X) is obtained by totalizing the number of cells which are selected from the group consisting of an endodermal cell, an ectodermal cell, and a mesodermal cell and are used as cells derived from a stem cell.

Note that in the culture chamber 30 shown in FIG. 7, a plurality of culture spaces 31 (a plurality of spaces in which cells are movable) are connected to each other with the medium 8. This makes it possible to easily set the same conditions, such as the medium 8, for each culture space 31.

The culture space 31 (the range of the culture space 31) will now be described with reference to FIGS. 2, 6, and 8 to 10. FIG. 7 illustrates an example in which the culture space 31 matches the space in which the cells are movable. However, the culture space does not necessarily match the space in which the cells are movable.

Figure 8:
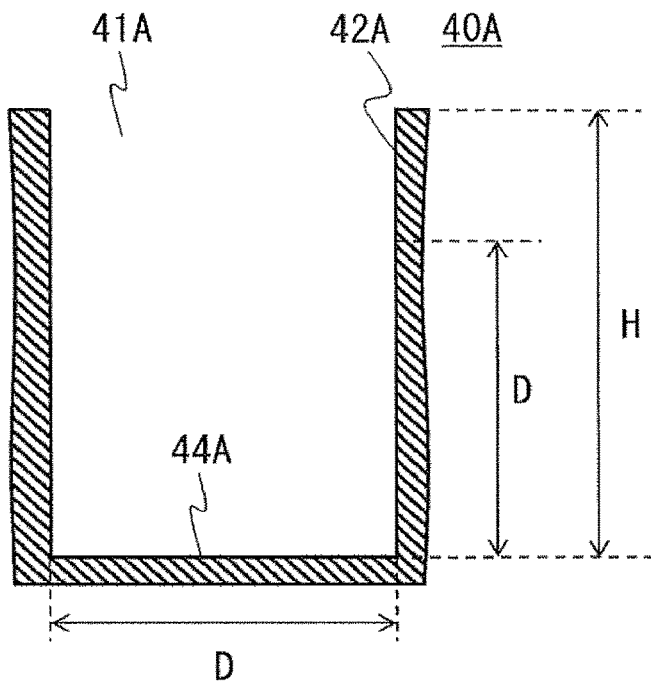
FIG. 8 is a diagram showing another example of the culture chamber.

For example, in a culture chamber 40A shown in FIG. 8, the height H of a wall 42A which forms the culture space 41A is larger than the equivalent diameter D (H>D). In this case, in the culture space 41A, a space from a bottom culture surface 44A to the height corresponding to the equivalent diameter D is used as the space in which the cells are movable. In other words, the height H of the space in which the cells are movable is limited to the equivalent diameter D or less.

In the culture chamber 10 shown in FIG. 2, the space in which the cells are movable extends to the height H1. In FIG. 2, the opening 12 is excluded from the culture space and the bottom portion 11 is used as the culture space.

Like the opening 12 of the recess 20D (culture chamber) shown in FIG. 6, when the opening has a uniform slope, the height of the culture space is set to a height at which the volume of the culture space is equal to or less than 400 mm$^3$. A space located at a position lower than the height is used as the space in which the cells are movable.

Figure 9:
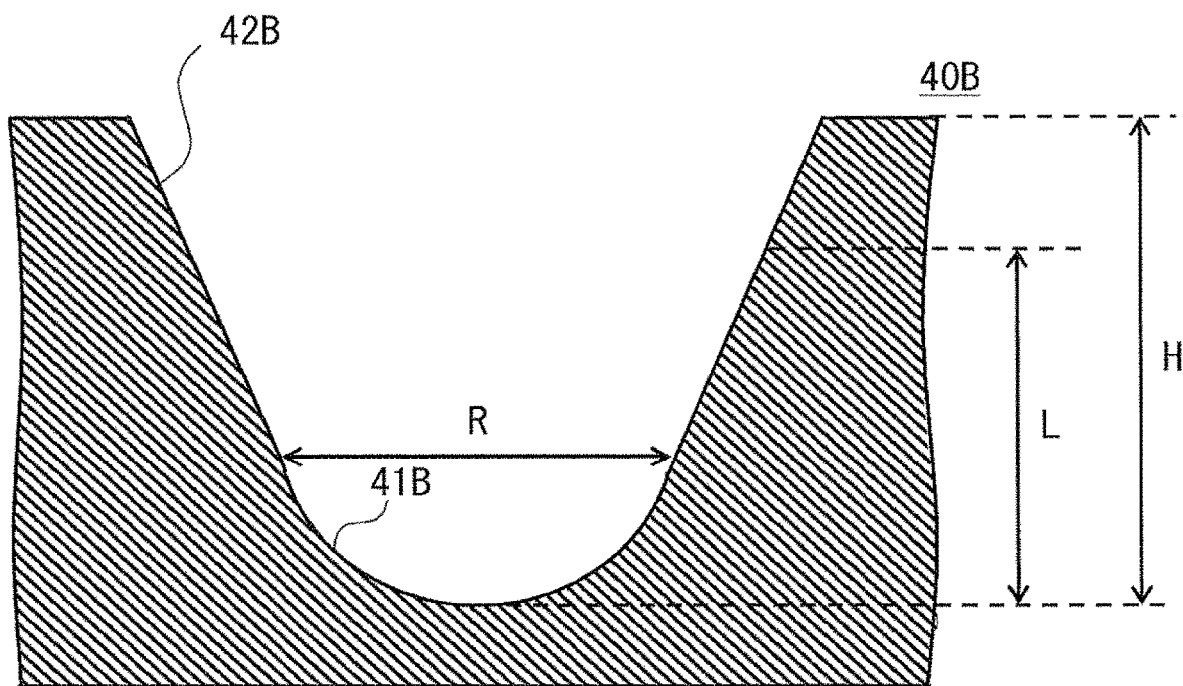
FIG. 9 is a diagram showing a further example of the culture chamber.

Additionally, a culture chamber 40B shown in FIG. 9 does not have a boundary between the bottom portion 11 and the opening 12, unlike in FIG. 2. Accordingly, the culture chamber is formed of a wall surface where a bottom portion 41B and an opening 42B have a uniform slope. In this case, the height of the culture space is set to a height at which the volume of the culture space is 400 mm$^3$ or less (e.g., L). Further, the space located at a position lower than the height is used as the space in which the cells are movable.

Figure 10:
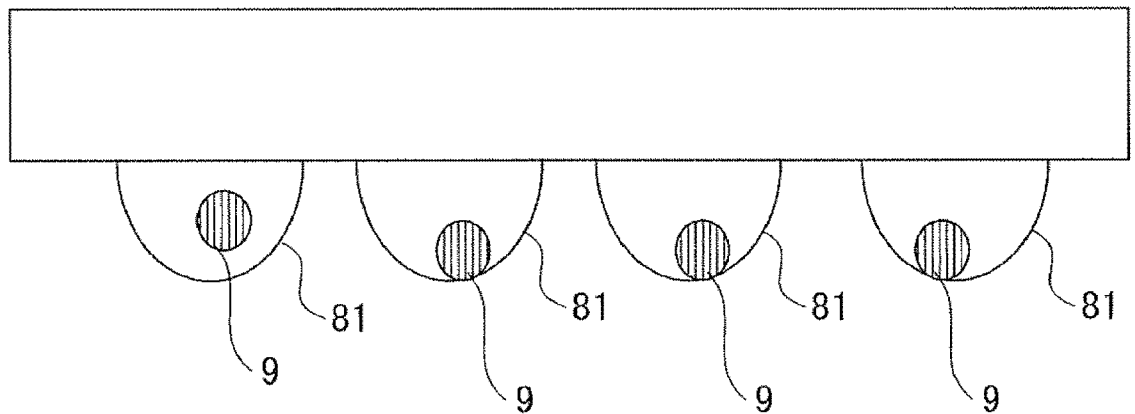
FIG. 10 is a diagram showing an example of a hanging drop method.

Furthermore, the space (culture space) in which the cells are movable is not necessarily surrounded by the culture chamber, for example, as in the case of using the hanging drop method (e.g., FIG. 10). In this case, the culture space is limited by a droplet 81 which is formed of a medium. Accordingly, the volume of the space in which the cells are movable is equal to the volume of the droplet 81.

The cells for forming a cell cluster are co-cultured in each recess 10 of the culture chamber 1 or in the culture space of the culture chamber 30. A space formed of a recess (a bottom portion of a recess) is the space in which the cells are movable, like the culture space. A chamber that forms the recess and the culture space (e.g., a chamber formed of the bottom culture surface 34 and the wall 32 in the culture chamber 30) is also referred to as a microchamber.

The microchamber is preferably formed as follows.

The equivalent diameter of the microchamber is preferably in a range from 20 μm to 2.5 mm. The depth of the microchamber is preferably in a range from 20 μm to 2.5 mm. To supply nutrients to a central portion of a cell cluster, the equivalent diameter is preferably in a range from 50 μm to 500 μm, and more preferably in a range from 100 μm to 500 μm.

The cell cluster is preferably cultured using a microchamber having a cell non-adhesive surface.

In order to form the cell cluster, it is preferable that the adhesion between the cells be promoted while preventing the cells from adhering to the culture surface. The culture chamber has a culture surface in contact with a cell. Accordingly, it is preferable that a polymer having cell non-adhesive properties is coated on the culture surface. The polymer is preferably selected from the group consisting of a phospholipid, a phospholipid-polymer complex, poly(2-hydroxyethyl methacrylate) (PHEMA), polyvinyl alcohol, agarose, chitosan, polyethyleneglycol, and albumin, or a combination thereof.

It is preferable that the culture chamber have a function for assisting culture and collection of cells, a function for holding a cell cluster, and a function for preventing removal of the cells during replacement of the medium. Thus, each recess 10 is preferably formed of the bottom portion 11 and the opening 12.

The opening 12 preferably includes a wall which extends from the boundary between the bottom portion 11 and the opening 12 to an upper end of the opening 12 and has a taper angle in a range from 1 degree to 20 degrees. The space of the opening 12 is preferably surrounded by the wall.

In order to aggregate the cells by their own weights at one location on the bottom portion 11, it is preferable that the space of the bottom portion 11 have a hemispherical shape or a truncated cone shape. According to this mode, the formation of a cell cluster can be promoted.

The cell cluster prepared as described above can be used for, for example, drug discovery screening and regenerative medicine.

To differentiate an undifferentiated cell and obtain a cell having functions similar to those in vivo, it is necessary to culture the undifferentiated cell to form a three-dimensional cell cluster. Further, a predetermined number of mesenchymal cells have been required to aggregate the cells and cause the cells to differentiate into an organ bud (e.g., Patent Literature 3). Meanwhile, this causes a problem that mesenchymal stem cells have an adverse effect on the differentiation of undifferentiated cells. For example, there is a problem that even when a fibrous cell or a bone cell is a cell of an organ other than the transplantation target, an undifferentiated cell differentiates into these cells (Non Patent Literature 2). Accordingly, a problem to be solved by the technique of culturing undifferentiated cells is to reduce the number of mesenchymal cells. However, in order to create a cell cluster, it is necessary to culture a predetermined number of mesenchymal cells, as well as triploblastic cells derived from a stem cell.

To differentiate an undifferentiated cell, it is necessary to form a cell cluster. Accordingly, it has been considered that it is extremely difficult to reduce the number of mesenchymal cells. However, the present inventors have found a technique capable of preparing a cell cluster even when the number of mesenchymal cells is reduced. In other words, the present inventors have found a technique for preparing a cell cluster. In the technique, the space in which cells are movable is limited and the density of mesenchymal cells is specified. Accordingly, a cell cluster can be prepared even when the number of mesenchymal cells is reduced as compared with the conventional case. Preparation of a cell cluster in a state where the number of mesenchymal cells is reduced as compared with the conventional case makes it possible to culture cells which have functions similar to those in vivo and do not differentiate into a tissue of an organ other than the transplantation target. Additionally, the culture method according to an embodiment does not require any complicated process. Therefore, a safe cell cluster can be efficiently obtained. Consequently, the time and cost required for obtaining a cell cluster can be reduced.

For example, techniques related to an artificial tissue have been developed on the basis of the technique of forming an organ bud as disclosed in Patent Literature 3. These techniques can provide various highly functional implants. In the techniques, the functions of an organ of interest are comprehensively grasped. The techniques aim to reproduce these functions by an artificial tissue. It is expected that the method according to the embodiment described above can be applied to these techniques. Additionally, in order to achieve an implant which exerts a plurality of such cell functions at the same time, there is a need for an artificial tissue which has matured to such a degree that the artificial tissue has functions similar to those in vivo. There is also a need for a method for enhancing the efficiency of differentiation of cells to obtain such an artificial tissue. Furthermore, a low-risk artificial tissue is required. The risk is that, for example, even when a fibrous cell or a bone cell is a cell of an organ other than the transplantation target, a cell of a transplanted artificial tissue may differentiate into these cells. It is expected that the culture method according to an embodiment is employed as a means for solving these problems.

Examples of test results obtained by carrying out one mode of the culture method according to the present invention will be described below.

Example 1 and Comparative Example 1

Example 1 and Comparative Example 1 were compared. Comparative Example 1 differs from Example 1 in that the space in which cells are movable is larger than 400 mm$^3$.
(1) Preparation of a Triploblastic Cell Derived from a Stem Cell A human iPS cell (human skin-derived TkDA3 hiPSC clone (provided by Mr. Koji Eto and Mr. Hiromitsu Nakauchi))) was cultured in an activin-supplemented serum-free medium, to thereby induce CXCR4- and E-cadherin-positive endodermal cells. BMP4 and FGF2 were added to the obtained endodermal cells and the endodermal cells were cultured for two days. As a result, a CXCR4-negative and HNF4α-positive hepatic endoderm cell population (liver endodermal cell) was obtained. The expressions of CXCR4 and HNF4α were confirmed by immunostaining and gene expression analysis in accordance with the description in the following document.

Karim Si-Tayeb, et. al., "Highly Efficient Generation of Human Hepatocyte-Like Cells from Induced Pluripotent Stem Cells", Hepatology, Vol 51, No. 1, 2010, pp. 297-305
(2) Adjustment and Culture of Cell Suspension The cell suspension was adjusted using the obtained liver endodermal cell, vascular endothelial cell (human umbilical cord blood-derived vein endothelial cell) (Lonza, Basel, Switzerland), and undifferentiated mesenchymal cell (human mesenchymal stem cell, which is hereinafter also referred to as MSC (mesenchymal stem cell)) (Lonza, Basel, Switzerland).

Figure 11:
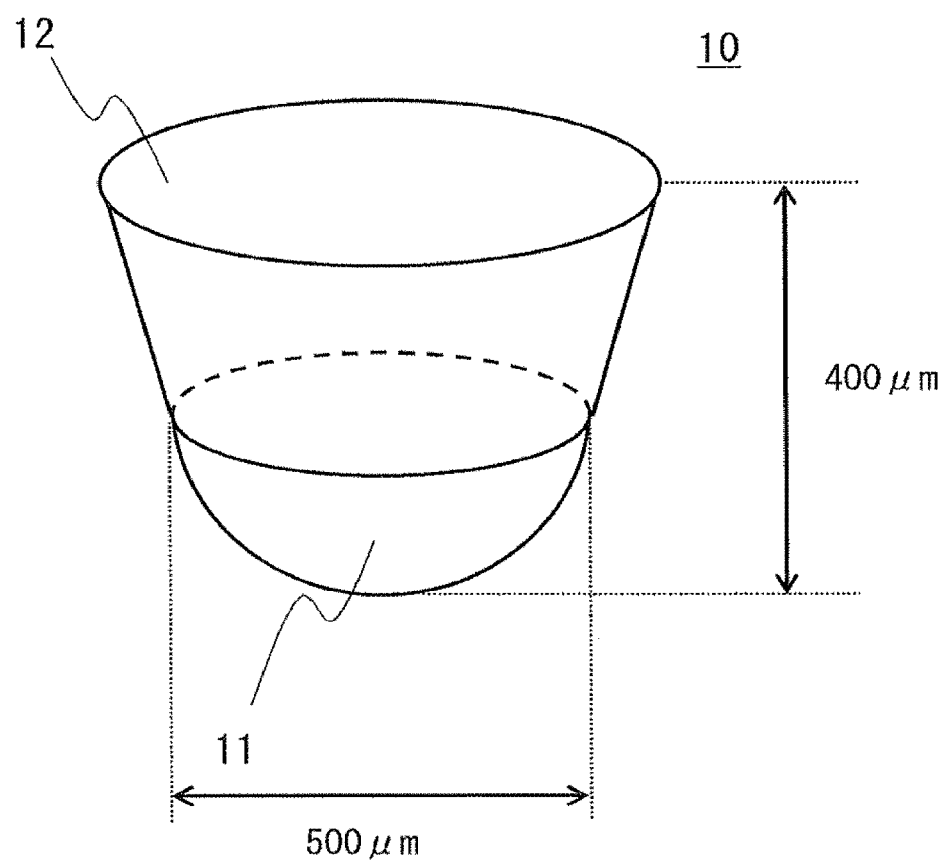
FIG. 11 is a diagram showing a culture chamber used in Examples.

The cell seeding ratio, i.e., (liver endodermal cells): (vascular endothelial cells):(undifferentiated mesenchymal cells), was set to 20:14:2, and the cells were mixed at this ratio, thereby preparing the cell suspension (cell solution). As the medium, endothelial cell medium kit-2: EGM-2 BulletKit (product code CC-3162: Lonza) was used. The cells were cultured for 20 days and the medium was replaced twice a week.
(3) Culture Chamber In Example 1, a recess (space, micro-space) in which the equivalent diameter of the space in which cells are movable is 500 μm and the depth thereof is 400 μm was used. A culture chamber of a 24-well plate including 600 recesses in one cell was used. FIG. 11 shows a culture chamber (recess 10) used in Example. The recess 10 is formed of the bottom portion 11 having a spherical shape with an equivalent diameter of 500 μm and the opening 12. The volume V of the space of the culture chamber in which cells are movable was 0.068 mm$^3$. To suppress the cell adhesion properties, p-HEMA was coated on the culture surface in contact with a cell.

In Comparative Example 1, cells were cultured in such a manner that the medium which was placed at a height of 3 mm from the culture surface in the 24-well plate with a bottom area of 2 cm$^2$ (200 mm$^2$). At this time, the volume of the space in which cells are movable was 600 mm$^3$. To suppress the cell adhesion properties, p-HEMA was coated on the culture surface in contact with a cell.
(4) The Number of Seeded Cells In each of 24 wells, $2.0 \times 10^5$ liver endodermal cells, $1.4 \times 10^5$ vascular endothelial cells, and $2.0 \times 10^4$ undifferentiated mesenchymal cells were seeded. The N/V ratio in Example was $2.0 \times 10^4 \div 600 \div 0.068 = 490$, and the N/V ratio in Comparative Example was $2.0 \times 10^4 \div 600 = 33$.

Figure 12:
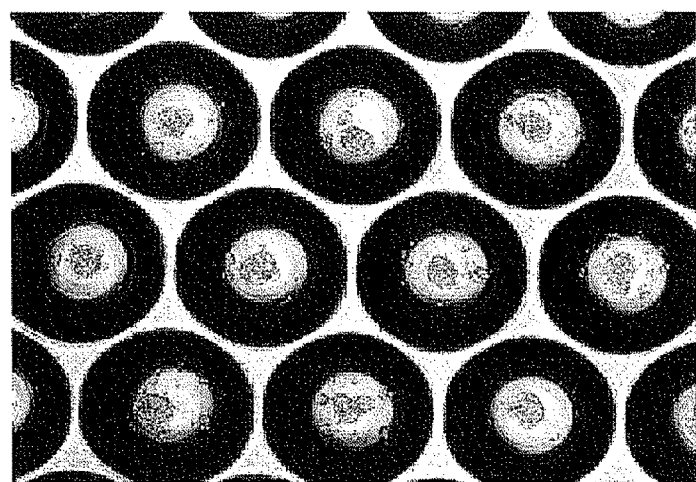
FIG. 12 is a photograph showing a result of a test in Example 1.

As described above, the N/V ratio is the ratio of the volume V (mm$^3$) of the space in which cells are movable to the cell number N of mesenchymal cells. In this case, the number of undifferentiated mesenchymal cells corresponds to the value N.
(5) Analysis On the 20th day of culture, cells in each well were observed from every field of view by magnifying them 10 times using an inverted microscope.
(6) Results In Comparative Example 1, almost no cell cluster was formed. On the other hand, in Example 1, as shown in FIG. 12, a cell cluster was formed. A cell cluster was formed in 500 spaces out of 600 spaces.

Example 2 and Comparative Example 2

Example 2 and Comparative Example 2 were compared. Comparative Example 2 differs from Example 2 in that the space in which cells are movable is equal to or less than 400 mm$^3$ and the N/V ratio is less than 31.
(1) Preparation of a Triploblastic Cell Derived from a Stem Cell A human iPS cell (human skin-derived TkDA3 hiPSC clone (provided by Mr. Koji Eto and Mr. Hiromitsu Nakauchi))) was cultured in an activin-supplemented serum-free medium, to thereby induce CXCR4- and E-cadherin-positive endodermal cells. The obtained endodermal cells were cultured in the presence of added BMP4 and FGF2 for two days to thereby obtain a CXCR4-negative and HNF4α-positive hepatic endoderm cell population. The expressions of CXCR4 and HNF4α were confirmed by immunostaining and gene expression analysis in the same manner as that in Example 1.
(2) Culture Chamber In Example 2 and Comparative Example 2, a recess (space) in which the equivalent diameter of the space in which cells are movable is 500 μm and the depth thereof is 400 μm was used. A culture chamber of a 24-well plate including 600 recesses was used. The overview of the culture chamber is the same as that of FIG. 11 described in Example 1. The volume V of the space of the culture chamber in which cells are movable was 0.068 mm$^3$. To suppress the cell adhesion properties, p-HEMA was coated on the culture surface in contact with a cell.
(3) Adjustment and Culture of Cell Suspension The cell suspension was adjusted using the obtained liver endodermal cell, vascular endothelial cell (human umbilical cord blood-derived vein endothelial cells) (Lonza, Basel, Switzerland), and undifferentiated mesenchymal cell (human mesenchymal stem cell) (Lonza, Basel, Switzerland).

Each cell suspension was adjusted to a cell seeding ratio shown in Table 1, and the cell suspension was seeded in a medium. As the medium, endothelial cell medium kit-2: EGM-2 BulletKit (product code CC-3162: Lonza) was used. The cells were cultured for 20 days and the medium was replaced twice a week.

TABLE 1

| | | Experimental conditions (the number of cells per well) | | | |
|---|---|---|---|---|---|
| | Notation in FIGURE | vascular endothelial cells | liver endodermal cells | un-differentiated mesenchymal cells | N/V |
| Example | MSC 1/10 | 1.4E+05 | 2.0E+05 | 2.0E+04 | 490.2 |
| | MSC 1/20 | 1.4E+05 | 2.0E+05 | 1.0E+04 | 245.1 |
| | MSC 1/40 | 1.4E+05 | 2.0E+05 | 5.0E+03 | 122.5 |
| | MSC 1/80 | 1.4E+05 | 2.0E+05 | 2.5E+03 | 61.3 |
| Comparative Example | MSC 1/160 | 1.4E+05 | 2.0E+05 | 1.3E+03 | 30.6 |
| | MSC 1/320 | 1.4E+05 | 2.0E+05 | 6.3E+02 | 15.3 |
| | MSC 1/640 | 1.4E+05 | 2.0E+05 | 3.1E+02 | 7.7 |
| | MSC 1/1280 | 1.4E+05 | 2.0E+05 | 1.6E+02 | 3.8 |

(4) Analysis

On the 20th day of culture, cells in each well were observed by magnifying them 10 times using an inverted microscope. All the 600 spots present in one well were observed. The number of spots in which a cell cluster of 10 or more cells in the well was formed was visually counted.

Two types of genes of HNF4a were selected using a hepatic differentiation marker AFP as an undifferentiation marker. These genes were analyzed by a real-time PCR method. To more specifically analyze the functions, ALB (albumin) transthyretin (TTR) ASGR1 (parenchymal hepatocytes) was selected as a hepatic differentiation marker. These functions were also analyzed by the real-time PCR method.

(5) Results

Cell Cluster Formation Efficiency

Figure 13:
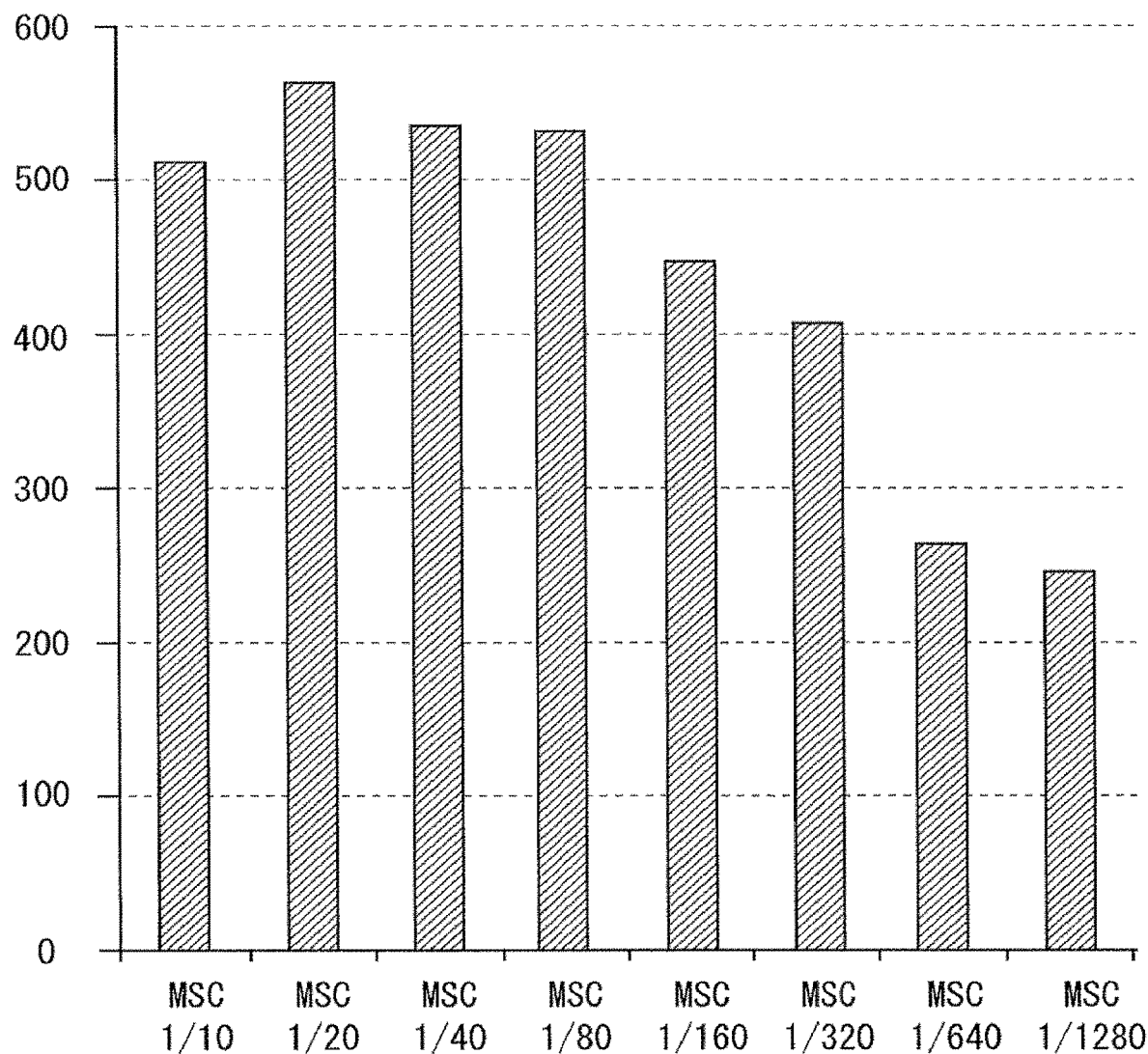
FIG. 13 is a graph showing a result of measuring the number of formed cell clusters in Example 2.

FIG. 13 is a graph showing a result of counting the number of formed cell clusters. The horizontal axis represents an MSC ratio, and the vertical axis represents the counted number of formed cell clusters. In Example, the MSC ratio was in a range from 1/80 to 1/10. The value of the N/V ratio was in a range from 61.3 to 490.2. In Example, a cell cluster was formed in 80% or more of 600 spots. When the MSC ratio was equal to or less than 1/160 and the value of the N/V ratio was equal to or less than 30.6, the formation percentage of a cell cluster was less than 80%. Especially, when the value of the N/V ratio was smaller than 30, the formation percentage of a cell cluster was drastically lowered.

Cell Function Evaluation (Gene Expression Analysis)

Figure 14:
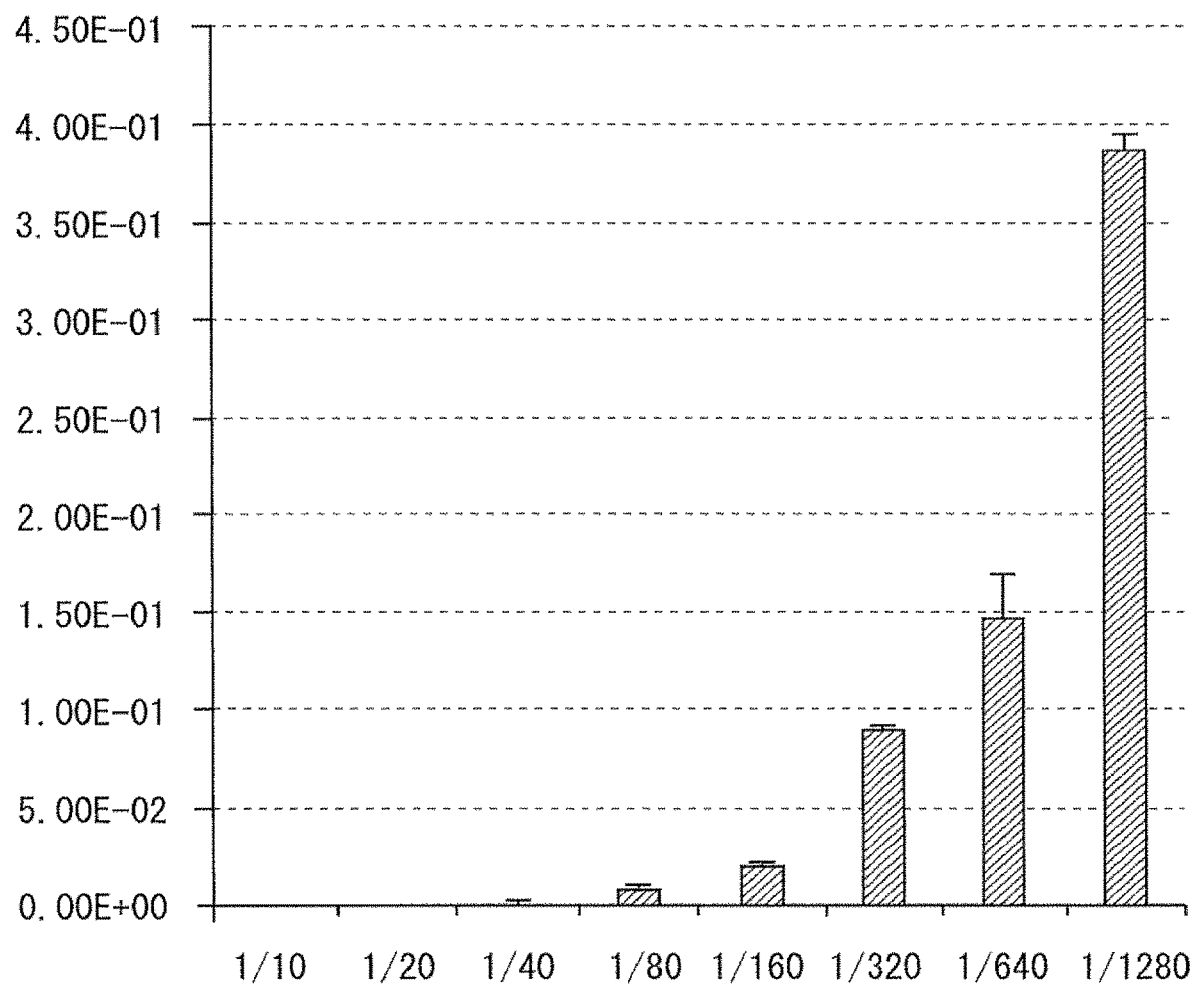
FIG. 14 is a graph showing a result of measuring an AFP expression level in Example 2.
Figure 15:
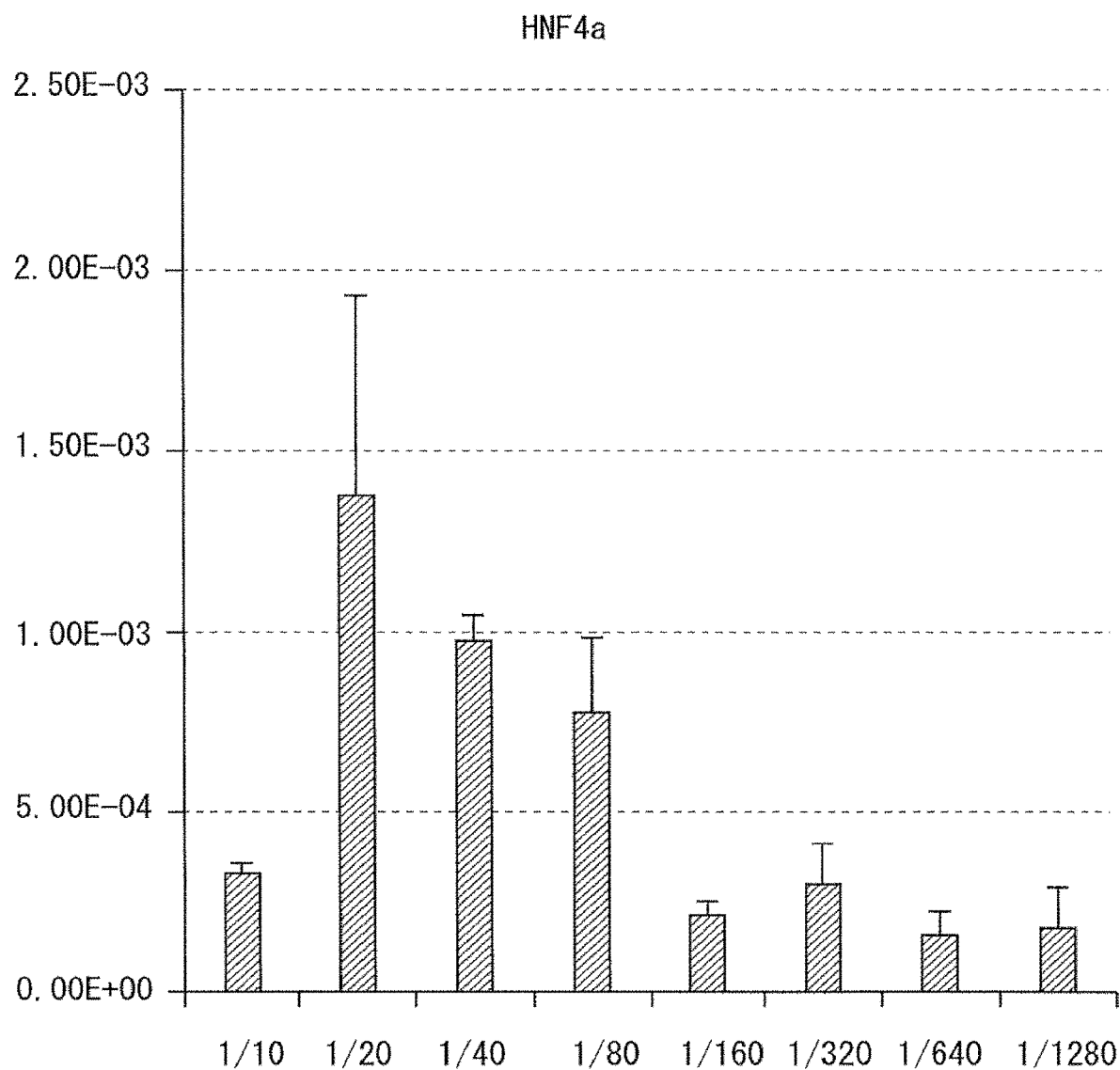
FIG. 15 is a graph showing a result of measuring an HNF4a expression level in Example 2.

FIG. 14 is a graph showing a result of measuring the AFP expression level, and FIG. 15 is a graph showing a result of measuring the HNF4a expression level. The horizontal axis in FIGS. 14 and 15 represents the MSC ratio, like in FIG. 13. The vertical axis represents the expression level (relative expression) of AFP or HNF4a. AFP is a gene that is specifically expressed in a juvenile cell. HNF4a is a gene that is specifically expressed in a mature cell.

In Example, the MSC ratio is in a range from 1/80 to 1/10. Under this condition, a cell cluster was formed in more than 80% of the spots. Further, HNF4a was expressed in the cell cluster. In Example, when the MSC ratio is in a range from 1/80 to 1/20, a cell cluster is formed in more than 80% of the spots, the expression level of HNF4a is high, and the expression level of AFP is low (substantially zero). The MSC ratio within this range represents a more preferable condition.

Further, the cell cluster was verified on a plurality of markers by changing the MSC ratio between 1/80 and 1/10. The gene expression levels of ALB (albumin), ASGR1 (parenchymal hepatocytes), and TTR (transthyretin), which are related to three functions included in a mature liver tissue, were analyzed.

Figure 16:
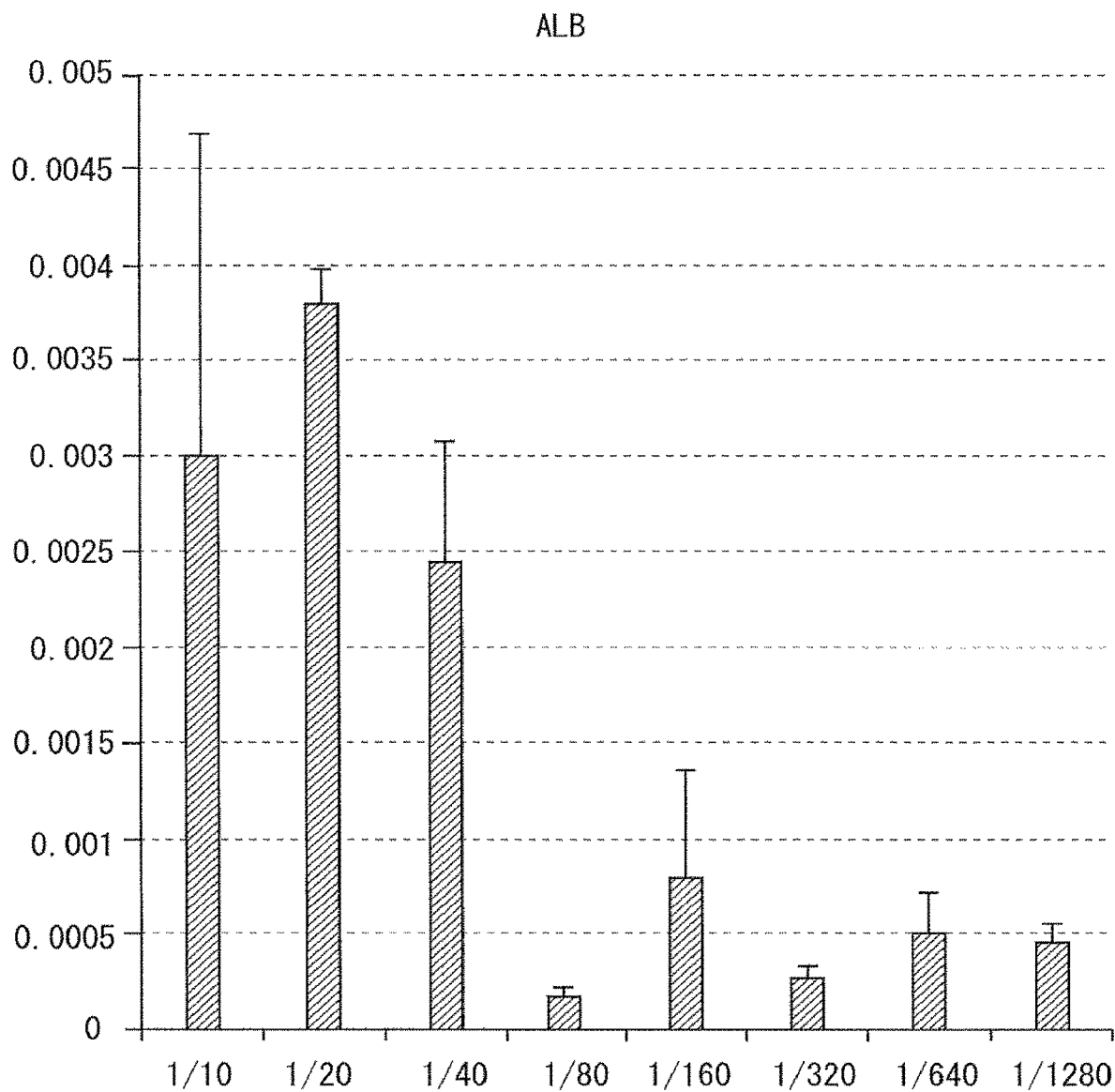
FIG. 16 is a graph showing a result of measuring an ALB expression level in Example 2.
Figure 17:
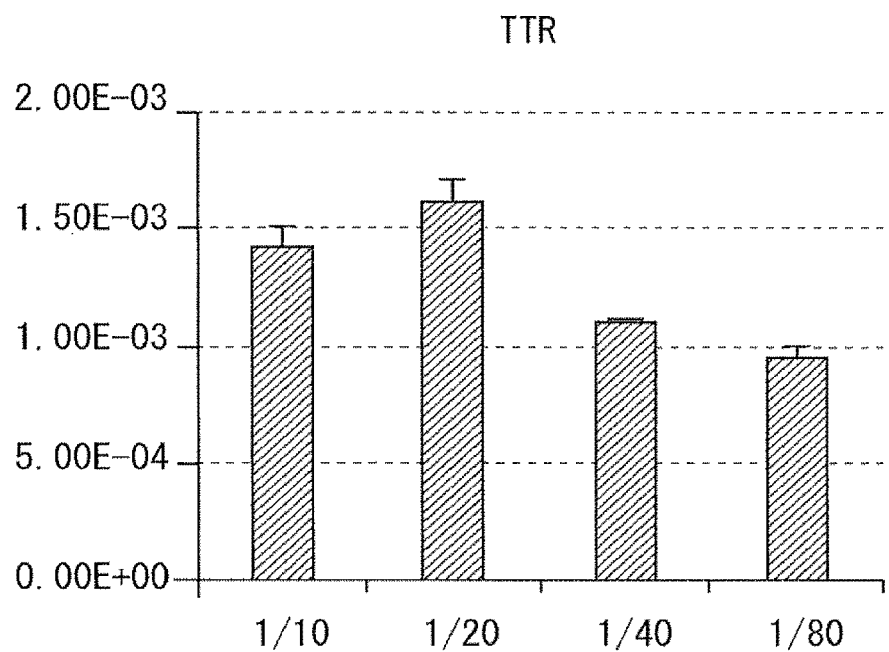
FIG. 17 is a graph showing a result of measuring a TTR expression level in Example 2.
Figure 18:
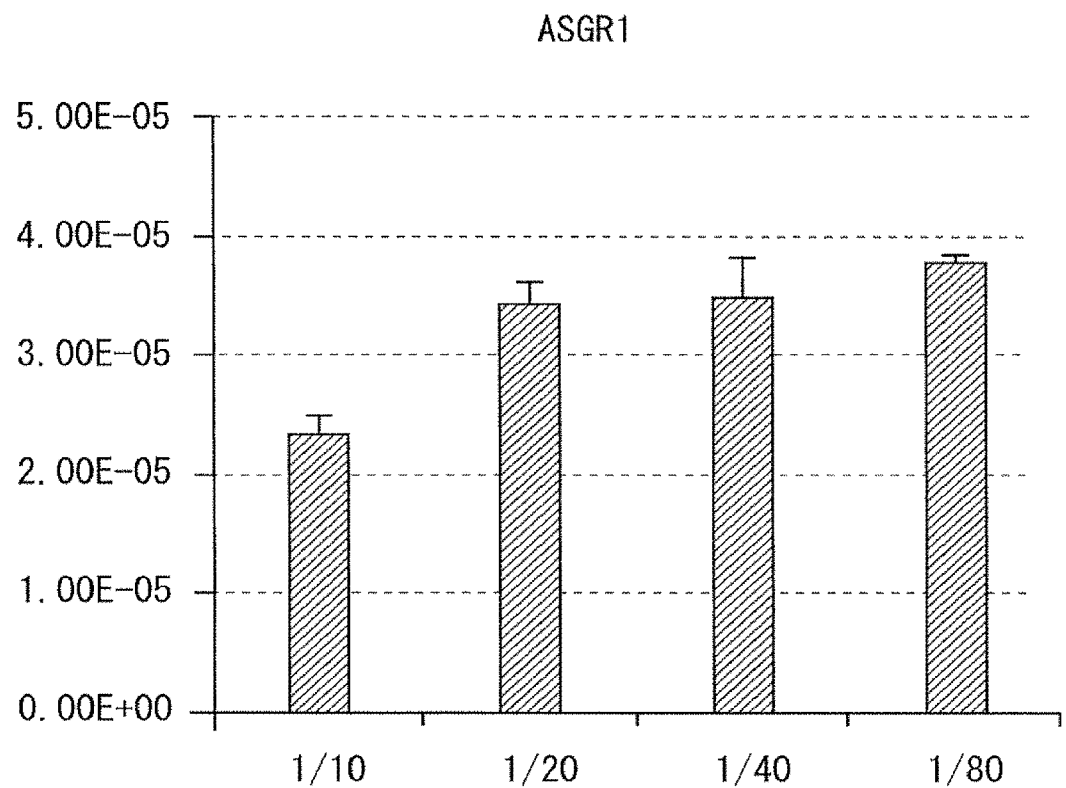
FIG. 18 is a graph showing an ASGR1 expression level in Example 2.

FIG. 16 is a graph showing a result of measuring the ALB expression level. FIG. 17 is a graph showing a result of measuring the TTR expression level. FIG. 18 is a graph showing a result of measuring the ASGR1 expression level. Like in FIG. 13, the horizontal axis in FIGS. 16 to 18 represents the MSC ratio. The vertical axis represents the expression level (relative expression) of ALB, TTR, or ASGR1.

In Table 2, "+" represents a minimum value in the values obtained under the conditions of the MSC ratio in a range from 1/80 to 1/10. In the table, the minimum value is represented by (+). A value which is equal to or less than twice the minimum value is represented by "++". A value which is from 2 to 4 times the minimum value is represented by "+++". A value which is greater than 4 times the minimum value is represented by "++++".

TABLE 2

| | MSC 1/10 | MSC 1/20 | MSC 1/40 | MSC 1/80 |
|---|---|---|---|---|
| HNF4a | (+) | +++ | ++ | ++ |
| ALB | ++++ | ++++ | ++++ | (+) |
| TTR | ++ | ++ | ++ | (+) |
| ASGR1 | (+) | ++ | ++ | ++ |

As shown in FIGS. 16 to 18 and Table 2, when the MSC ratio was 1/20 and 1/40, the gene expression levels of all the differentiation markers showed significantly high values.

This application is based upon and claims the benefit of priority from Japanese patent application No. 2014-112959, filed on May 30, 2014, the disclosure of which is incorporated herein in its entirety by reference.

REFERENCE SIGNS LIST 1, 30, 40A, 40B CULTURE CHAMBER
3 CULTURE PLATE
8 MEDIUM
9 CELL CLUSTER
10, 20D RECESS
11, 41B BOTTOM PORTION
12, 42B OPENING
31, 41A CULTURE SPACE
32, 42A WALL
33 BOTTOM PORTION
34, 44A BOTTOM CULTURE SURFACE
81 DROPLET

The invention claimed is:

1. A culture method comprising:
three-dimensionally culturing a population including two or more cells in an area, the population including at least one cell derived from a stem cell wherein the stem cell is selected from the group consisting of an undifferentiated endodermal cell, an undifferentiated ectodermal cell, and an undifferentiated mesodermal cell; and at least one mesenchymal cell, wherein:

the area is formed of a microchamber comprising:
a bottom portion including a space in which cells are movable, the space having a hemispherical shape;
an opening portion having a horn shape formed with a tapered wall;
a boundary portion where the bottom portion and the opening portion are in contact, the boundary portion having a diameter; and
a culture surface in contact with the cells, and the culture surface is coated with a polymer selected from the group consisting of a phospholipid, a phospholipid-polymer complex, poly(2-hydroxyethyl methacrylate) (PHEMA), polyvinyl alcohol, agarose, chitosan, polyethyleneglycol, and albumin, or a combination thereof, wherein
the bottom portion has a height equal to half of the diameter of the boundary portion, and the opening has a height equal to or smaller than the height of the bottom portion; and
when the space has a volume of V mm$^3$ and the number of the mesenchymal cells seeded in the space is represented by N, the V is equal to or less than 400 and N/V is in a range from 35 to 3000.

2. The culture method according to claim 1, further comprising performing the three-dimensional culture of the population together with at least one of: a vascular cell; a factor autonomously secreted from a vascular cell; or a factor secreted from a vascular cell due to the presence of both a vascular cell and a mesenchymal cell.

3. The culture method according to claim 1, wherein a ratio of the number of the mesenchymal cells to a total number of cells used for culture is 0.5% or more but less than 5%.

4. The culture method according to claim 1, wherein the population includes a cell number X of the cells derived from a stem cell and a cell number Y of the mesenchymal cells, and the X:Y is in a range from 20:1 to 100:1.

5. The culture method according to claim 4, wherein
the N/V is in a range from 100 to 300,
the X:Y is in a range from 20:1 to 50:1,
the V is equal to or less than 1, and
when an equivalent diameter of the microchamber is represented by E and a depth of the microchamber is represented by D, E:D is in a range from 1:0.5 to 1:1.

6. The culture method according to claim 1, wherein a cell cluster obtained by the three-dimensional culture is an organ bud.

7. The culture method according to claim 1, wherein a cell cluster obtained by the three-dimensional culture has a spheroid shape, and the cell cluster having the spheroid shape has a diameter in a range from 20 μm to 2 mm.

8. The culture method according to claim 1, wherein the cell derived from a stem cell is derived from a fetal stem cell or an induced pluripotent stem cell.

9. The culture method according to claim 1, wherein
the cell derived from a stem cell is derived from an induced pluripotent stem cell, and
the cell derived from a stem cell is an endodermal cell.

10. The culture method according to claim 1, wherein
an equivalent diameter of the microchamber is in a range from 20 μm to 2.5 mm, and
a depth of the microchamber is in a range from 20 μm to 1000 μm.

11. The culture method according to claim 10, wherein
the tapered wall has a taper angle in a range from 1 to 20 degrees, and
a plurality of the microchambers are arranged on a bottom of a well, wherein the opening portion with the tapered wall supports transferring cells from the bottom portion of the microchamber into the well.

12. The culture method according to claim 1, wherein the polymer is poly(2-hydroxyethyl methacrylate) (PHEMA).

13. A culture method comprising three-dimensionally culturing a population including two or more cells in an area, the population including a cell number X of a liver endodermal cell, a vascular endothelial cell, and a cell number Y of a mesenchymal cell, wherein:
the area is formed of a microchamber comprising:
a bottom portion including a space in which cells are movable, the space having a hemispherical shape;
an opening portion having a horn shape formed with a tapered wall;
a boundary portion where the bottom portion and the opening portion are in contact, the boundary portion having a diameter; and
a culture surface in contact with the cells, and the culture surface is coated with a polymer selected from the group consisting of a phospholipid, a phospholipid-polymer complex, poly(2-hydroxyethyl methacrylate) (PHEMA), polyvinyl alcohol, agarose, chitosan, polyethyleneglycol, and albumin, or a combination thereof, wherein
the bottom portion has a height equal to half of the diameter of the boundary portion, and the opening has a height equal to or smaller than the height of the bottom portion; and
when the space has a volume of V mm$^3$ and the number of the mesenchymal cells seeded in the space is represented by N,
Y/V is in a range from 122.5 to 490.2,
X:Y is in a range from 10:1 to 40:1,
V is equal to or less than 0.068, and
N/V is in a range from 35 to 3000.

14. The culture method according to claim 13, wherein a cell number of the vascular endothelial cell is Z, and X:Z is in a range from 10:5 to 10:10.

* * * * *